US011820991B2

(12) United States Patent
Zhang et al.

(10) Patent No.: US 11,820,991 B2
(45) Date of Patent: Nov. 21, 2023

(54) POLYPEPTIDE AND NUCLEIC ACID CAPABLE OF CHANGING AMYLOSE CONTENT (AC) IN PLANT, AND USE THEREOF

(71) Applicant: SHANDONG SHUNFENG BIOTECHNOLOGY CO., LTD., Jinan (CN)

(72) Inventors: Jinshan Zhang, Jinan (CN); Xiaorui Huang, Jinan (CN); Xiaomu Niu, Jinan (CN)

(73) Assignee: SHANDONG SHUNFENG BIOTECHNOLOGY CO., LTD., Jinan (CN)

( * ) Notice: Subject to any disclaimer, the term of this patent is extended or adjusted under 35 U.S.C. 154(b) by 106 days.

(21) Appl. No.: 17/454,486

(22) Filed: Nov. 11, 2021

(65) Prior Publication Data

US 2022/0195448 A1 Jun. 23, 2022

Related U.S. Application Data

(63) Continuation of application No. PCT/CN2021/099676, filed on Jun. 11, 2021.

(30) Foreign Application Priority Data

Jun. 15, 2020 (CN) .......................... 202010543417.8
Jul. 9, 2020 (CN) .......................... 202010657795.9
Feb. 23, 2021 (CN) .......................... 202110204689.X

(51) Int. Cl.
C12N 15/82 (2006.01)
C12N 9/10 (2006.01)
C07K 14/415 (2006.01)
C12N 15/11 (2006.01)

(52) U.S. Cl.
CPC ........ *C12N 15/8245* (2013.01); *C07K 14/415* (2013.01); *C12N 9/1051* (2013.01); *C12N 15/111* (2013.01); *C12N 15/8216* (2013.01); *C12Y 204/01011* (2013.01); *C12N 2310/20* (2017.05)

(58) Field of Classification Search
None
See application file for complete search history.

(56) References Cited

U.S. PATENT DOCUMENTS 8,252,975 B2 * 8/2012 Frohberg ........... C12N 15/8245
435/468

FOREIGN PATENT DOCUMENTS

| CN | 103695381 A | 4/2014 |
| CN | 105400748 A | 3/2016 |
| CN | 110714010 A | 1/2020 |
| CN | 11197034 A | 5/2020 |

OTHER PUBLICATIONS

Perez et al Plant Cell Reports 38:417-433 (Year: 2019).*
GenBank: XP_015644490.1, granule-bound starch synthase 1, chloroplastic/amyloplastic isoform X2 [*Oryza sativa* Japonica Group], Aug. 2018.

* cited by examiner

*Primary Examiner* — Brent T Page
(74) *Attorney, Agent, or Firm* — Bayramoglu Law Offices LLC

(57) ABSTRACT

A mutant granule-bound starch synthase 1 (GBSS1) polypeptide and a nucleic acid, and use thereof are provided. Compared to an amino acid sequence of a parent GBSS1, the mutant GBSS1 polypeptide has a mutation at an amino acid corresponding to one or more of amino acid 237, amino acid 168, and amino acid 411 of an amino acid sequence shown in SEQ ID NO: 1. An amylose content (AC) in a plant changes after the plant undergoes GBSS1 mutation, which has very promising application prospects in the improvement of edible quality of rice.

19 Claims, 4 Drawing Sheets

Specification includes a Sequence Listing.

SEQUENCE LISTING

<160> NUMBER OF SEQ ID NOS: 23

<210> SEQ ID NO 1
<211> LENGTH: 609
<212> TYPE: PRT
<213> ORGANISM: Artificial Sequence
<220> FEATURE:
<223> OTHER INFORMATION: Amino acid sequence of Oryza sativa wild-type
      GBSS1

<400> SEQUENCE: 1

Met Ser Ala Leu Thr Thr Ser Gln Leu Ala Thr Ser Ala Thr Gly Phe
1               5                   10                  15

Gly Ile Ala Asp Arg Ser Ala Pro Ser Ser Leu Leu Arg His Gly Phe
            20                  25                  30

Gln Gly Leu Lys Pro Arg Ser Pro Ala Gly Gly Asp Ala Thr Ser Leu
        35                  40                  45

Ser Val Thr Thr Ser Ala Arg Ala Thr Pro Lys Gln Gln Arg Ser Val
    50                  55                  60

Gln Arg Gly Ser Arg Arg Phe Pro Ser Val Val Val Tyr Ala Thr Gly
65                  70                  75                  80

Ala Gly Met Asn Val Val Phe Val Gly Ala Glu Met Ala Pro Trp Ser
                85                  90                  95

Lys Thr Gly Gly Leu Gly Asp Val Leu Gly Gly Leu Pro Pro Ala Met
            100                 105                 110

Ala Ala Asn Gly His Arg Val Met Val Ile Ser Pro Arg Tyr Asp Gln
        115                 120                 125

Tyr Lys Asp Ala Trp Asp Thr Ser Val Val Ala Glu Ile Lys Val Ala
    130                 135                 140

Asp Arg Tyr Glu Arg Val Arg Phe Phe His Cys Tyr Lys Arg Gly Val
145                 150                 155                 160

Asp Arg Val Phe Ile Asp His Pro Ser Phe Leu Glu Lys Val Trp Gly
                165                 170                 175

Lys Thr Gly Glu Lys Ile Tyr Gly Pro Asp Thr Gly Val Asp Tyr Lys
            180                 185                 190

Asp Asn Gln Met Arg Phe Ser Leu Leu Cys Gln Ala Ala Leu Glu Ala
        195                 200                 205

Pro Arg Ile Leu Asn Leu Asn Asn Pro Tyr Phe Lys Gly Thr Tyr
210                 215                 220

Gly Glu Asp Val Val Phe Val Cys Asn Asp Trp His Thr Gly Pro Leu
225                 230                 235                 240

Ala Ser Tyr Leu Lys Asn Asn Tyr Gln Pro Asn Gly Ile Tyr Arg Asn
            245                 250                 255

Ala Lys Val Ala Phe Cys Ile His Asn Ile Ser Tyr Gln Gly Arg Phe
            260                 265                 270

Ala Phe Glu Asp Tyr Pro Glu Leu Asn Leu Ser Glu Arg Phe Arg Ser
        275                 280                 285

Ser Phe Asp Phe Ile Asp Gly Tyr Asp Thr Pro Val Glu Gly Arg Lys
    290                 295                 300

Ile Asn Trp Met Lys Ala Gly Ile Leu Glu Ala Asp Arg Val Leu Thr
305                 310                 315                 320

Val Ser Pro Tyr Tyr Ala Glu Glu Leu Ile Ser Gly Ile Ala Arg Gly
                325                 330                 335

Cys Glu Leu Asp Asn Ile Met Arg Leu Thr Gly Ile Thr Gly Ile Val
            340                 345                 350

Asn Gly Met Asp Val Ser Glu Trp Asp Pro Ser Lys Asp Lys Tyr Ile
        355                 360                 365

Thr Ala Lys Tyr Asp Ala Thr Thr Ala Ile Glu Ala Lys Ala Leu Asn
370                 375                 380

Lys Glu Ala Leu Gln Ala Glu Ala Gly Leu Pro Val Asp Arg Lys Ile
385                 390                 395                 400

Pro Leu Ile Ala Phe Ile Gly Arg Leu Glu Glu Gln Lys Gly Pro Asp
                405                 410                 415

Val Met Ala Ala Ala Ile Pro Glu Leu Met Gln Glu Asp Val Gln Ile
            420                 425                 430

Val Leu Leu Gly Thr Gly Lys Lys Lys Phe Glu Lys Leu Leu Lys Ser
        435                 440                 445

Met Glu Glu Lys Tyr Pro Gly Lys Val Arg Ala Val Val Lys Phe Asn
    450                 455                 460

Ala Pro Leu Ala His Leu Ile Met Ala Gly Ala Asp Val Leu Ala Val
465                 470                 475                 480

Pro Ser Arg Phe Glu Pro Cys Gly Leu Ile Gln Leu Gln Gly Met Arg
                485                 490                 495

Tyr Gly Thr Pro Cys Ala Cys Ala Ser Thr Gly Gly Leu Val Asp Thr
            500                 505                 510

Val Ile Glu Gly Lys Thr Gly Phe His Met Gly Arg Leu Ser Val Asp
        515                 520                 525

Cys Lys Val Val Glu Pro Ser Asp Val Lys Lys Val Ala Ala Thr Leu
530                 535                 540

Lys Arg Ala Ile Lys Val Val Gly Thr Pro Ala Tyr Glu Glu Met Val
545                 550                 555                 560

Arg Asn Cys Met Asn Gln Asp Leu Ser Trp Lys Gly Pro Ala Lys Asn
                565                 570                 575

Trp Glu Asn Val Leu Leu Gly Leu Gly Val Ala Gly Ser Ala Pro Gly
            580                 585                 590

Ile Glu Gly Asp Glu Ile Ala Pro Leu Ala Lys Glu Asn Val Ala Ala
        595                 600                 605

Pro

<210> SEQ ID NO 2

```
<211> LENGTH: 609
<212> TYPE: PRT
<213> ORGANISM: Artificial Sequence
<220> FEATURE:
<223> OTHER INFORMATION: Amino acid sequence of P168L mutant GBSS1

<400> SEQUENCE: 2
```

Met Ser Ala Leu Thr Thr Ser Gln Leu Ala Thr Ser Thr Gly Phe
1               5                   10                  15

Gly Ile Ala Asp Arg Ser Ala Pro Ser Ser Leu Leu Arg His Gly Phe
            20                  25                  30

Gln Gly Leu Lys Pro Arg Ser Pro Ala Gly Gly Asp Ala Thr Ser Leu
        35                  40                  45

Ser Val Thr Thr Ser Ala Arg Ala Thr Pro Lys Gln Gln Arg Ser Val
50                  55                  60

Gln Arg Gly Ser Arg Arg Phe Pro Ser Val Val Val Tyr Ala Thr Gly
65                  70                  75                  80

Ala Gly Met Asn Val Val Phe Val Gly Ala Glu Met Ala Pro Trp Ser
                85                  90                  95

Lys Thr Gly Gly Leu Gly Asp Val Leu Gly Gly Leu Pro Pro Ala Met
            100                 105                 110

Ala Ala Asn Gly His Arg Val Met Val Ile Ser Pro Arg Tyr Asp Gln
        115                 120                 125

Tyr Lys Asp Ala Trp Asp Thr Ser Val Val Ala Glu Ile Lys Val Ala
130                 135                 140

Asp Arg Tyr Glu Arg Val Arg Phe Phe His Cys Tyr Lys Arg Gly Val
145                 150                 155                 160

Asp Arg Val Phe Ile Asp His Leu Ser Phe Leu Glu Lys Val Trp Gly
                165                 170                 175

Lys Thr Gly Glu Lys Ile Tyr Gly Pro Asp Thr Gly Val Asp Tyr Lys
            180                 185                 190

Asp Asn Gln Met Arg Phe Ser Leu Leu Cys Gln Ala Ala Leu Glu Ala
        195                 200                 205

Pro Arg Ile Leu Asn Leu Asn Asn Asn Pro Tyr Phe Lys Gly Thr Tyr
210                 215                 220

Gly Glu Asp Val Val Phe Val Cys Asn Asp Trp His Thr Gly Pro Leu
225                 230                 235                 240

Ala Ser Tyr Leu Lys Asn Asn Tyr Gln Pro Asn Gly Ile Tyr Arg Asn
                245                 250                 255

Ala Lys Val Ala Phe Cys Ile His Asn Ile Ser Tyr Gln Gly Arg Phe
            260                 265                 270

Ala Phe Glu Asp Tyr Pro Glu Leu Asn Leu Ser Glu Arg Phe Arg Ser
        275                 280                 285

Ser Phe Asp Phe Ile Asp Gly Tyr Asp Thr Pro Val Glu Gly Arg Lys
290                 295                 300

Ile Asn Trp Met Lys Ala Gly Ile Leu Glu Ala Asp Arg Val Leu Thr
305                 310                 315                 320

Val Ser Pro Tyr Tyr Ala Glu Glu Leu Ile Ser Gly Ile Ala Arg Gly
                325                 330                 335

Cys Glu Leu Asp Asn Ile Met Arg Leu Thr Gly Ile Thr Gly Ile Val
            340                 345                 350

Asn Gly Met Asp Val Ser Glu Trp Asp Pro Ser Lys Asp Lys Tyr Ile
        355                 360                 365

Thr Ala Lys Tyr Asp Ala Thr Thr Ala Ile Glu Ala Lys Ala Leu Asn
370                 375                 380

Lys Glu Ala Leu Gln Ala Glu Ala Gly Leu Pro Val Asp Arg Lys Ile
385                 390                 395                 400

Pro Leu Ile Ala Phe Ile Gly Arg Leu Glu Glu Gln Lys Gly Pro Asp
                405                 410                 415

Val Met Ala Ala Ala Ile Pro Glu Leu Met Gln Glu Asp Val Gln Ile
            420                 425                 430

Val Leu Leu Gly Thr Gly Lys Lys Lys Phe Glu Lys Leu Leu Lys Ser
        435                 440                 445

Met Glu Glu Lys Tyr Pro Gly Lys Val Arg Ala Val Val Lys Phe Asn
    450                 455                 460

Ala Pro Leu Ala His Leu Ile Met Ala Gly Ala Asp Val Leu Ala Val
465                 470                 475                 480

Pro Ser Arg Phe Glu Pro Cys Gly Leu Ile Gln Leu Gln Gly Met Arg
                485                 490                 495

Tyr Gly Thr Pro Cys Ala Cys Ala Ser Thr Gly Gly Leu Val Asp Thr
            500                 505                 510

Val Ile Glu Gly Lys Thr Gly Phe His Met Gly Arg Leu Ser Val Asp
        515                 520                 525

Cys Lys Val Val Glu Pro Ser Asp Val Lys Lys Val Ala Ala Thr Leu
530                 535                 540

Lys Arg Ala Ile Lys Val Val Gly Thr Pro Ala Tyr Glu Glu Met Val
545                 550                 555                 560

Arg Asn Cys Met Asn Gln Asp Leu Ser Trp Lys Gly Pro Ala Lys Asn
            565                 570                 575

Trp Glu Asn Val Leu Leu Gly Leu Gly Val Ala Gly Ser Ala Pro Gly
                580                 585                 590

Ile Glu Gly Asp Glu Ile Ala Pro Leu Ala Lys Glu Asn Val Ala Ala
            595                 600                 605

Pro

<210> SEQ ID NO 3
<211> LENGTH: 609
<212> TYPE: PRT
<213> ORGANISM: Artificial Sequence
<220> FEATURE:
<223> OTHER INFORMATION: Amino acid sequence of T237A mutant GBSS1

<400> SEQUENCE: 3

Met Ser Ala Leu Thr Thr Ser Gln Leu Ala Thr Ser Ala Thr Gly Phe
1               5                   10                  15

Gly Ile Ala Asp Arg Ser Ala Pro Ser Ser Leu Leu Arg His Gly Phe
                20                  25                  30

Gln Gly Leu Lys Pro Arg Ser Pro Ala Gly Gly Asp Ala Thr Ser Leu
            35                  40                  45

Ser Val Thr Thr Ser Ala Arg Ala Thr Pro Lys Gln Gln Arg Ser Val
        50                  55                  60

Gln Arg Gly Ser Arg Arg Phe Pro Ser Val Val Val Tyr Ala Thr Gly
65                  70                  75                  80

Ala Gly Met Asn Val Val Phe Val Gly Ala Glu Met Ala Pro Trp Ser
                85                  90                  95

Lys Thr Gly Gly Leu Gly Asp Val Leu Gly Gly Leu Pro Pro Ala Met
            100                 105                 110

Ala Ala Asn Gly His Arg Val Met Val Ile Ser Pro Arg Tyr Asp Gln
        115                 120                 125

```
Tyr Lys Asp Ala Trp Asp Thr Ser Val Val Ala Glu Ile Lys Val Ala
    130                 135                 140
Asp Arg Tyr Glu Arg Val Arg Phe Phe His Cys Tyr Lys Arg Gly Val
145                 150                 155                 160
Asp Arg Val Phe Ile Asp His Pro Ser Phe Leu Glu Lys Val Trp Gly
                165                 170                 175
Lys Thr Gly Glu Lys Ile Tyr Gly Pro Asp Thr Gly Val Asp Tyr Lys
            180                 185                 190
Asp Asn Gln Met Arg Phe Ser Leu Leu Cys Gln Ala Ala Leu Glu Ala
        195                 200                 205
Pro Arg Ile Leu Asn Leu Asn Asn Pro Tyr Phe Lys Gly Thr Tyr
210                 215                 220
Gly Glu Asp Val Val Phe Val Cys Asn Asp Trp His Ala Gly Pro Leu
225                 230                 235                 240
Ala Ser Tyr Leu Lys Asn Asn Tyr Gln Pro Asn Gly Ile Tyr Arg Asn
                245                 250                 255
Ala Lys Val Ala Phe Cys Ile His Asn Ile Ser Tyr Gln Gly Arg Phe
            260                 265                 270
Ala Phe Glu Asp Tyr Pro Glu Leu Asn Leu Ser Glu Arg Phe Arg Ser
        275                 280                 285
Ser Phe Asp Phe Ile Asp Gly Tyr Asp Thr Pro Val Glu Gly Arg Lys
    290                 295                 300
Ile Asn Trp Met Lys Ala Gly Ile Leu Glu Ala Asp Arg Val Leu Thr
305                 310                 315                 320
Val Ser Pro Tyr Tyr Ala Glu Glu Leu Ile Ser Gly Ile Ala Arg Gly
                325                 330                 335
Cys Glu Leu Asp Asn Ile Met Arg Leu Thr Gly Ile Thr Gly Ile Val
            340                 345                 350
Asn Gly Met Asp Val Ser Glu Trp Asp Pro Ser Lys Asp Lys Tyr Ile
        355                 360                 365
Thr Ala Lys Tyr Asp Ala Thr Thr Ala Ile Glu Ala Lys Ala Leu Asn
    370                 375                 380
Lys Glu Ala Leu Gln Ala Glu Ala Gly Leu Pro Val Asp Arg Lys Ile
385                 390                 395                 400
Pro Leu Ile Ala Phe Ile Gly Arg Leu Glu Glu Gln Lys Gly Pro Asp
                405                 410                 415
Val Met Ala Ala Ala Ile Pro Glu Leu Met Gln Glu Asp Val Gln Ile
            420                 425                 430
Val Leu Leu Gly Thr Gly Lys Lys Lys Phe Glu Lys Leu Leu Lys Ser
        435                 440                 445
Met Glu Glu Lys Tyr Pro Gly Lys Val Arg Ala Val Val Lys Phe Asn
    450                 455                 460
Ala Pro Leu Ala His Leu Ile Met Ala Gly Ala Asp Val Leu Ala Val
465                 470                 475                 480
Pro Ser Arg Phe Glu Pro Cys Gly Leu Ile Gln Leu Gln Gly Met Arg
                485                 490                 495
Tyr Gly Thr Pro Cys Ala Cys Ala Ser Thr Gly Gly Leu Val Asp Thr
            500                 505                 510
Val Ile Glu Gly Lys Thr Gly Phe His Met Gly Arg Leu Ser Val Asp
        515                 520                 525
Cys Lys Val Val Glu Pro Ser Asp Val Lys Lys Val Ala Ala Thr Leu
    530                 535                 540
Lys Arg Ala Ile Lys Val Val Gly Thr Pro Ala Tyr Glu Glu Met Val
```

```
                545                 550                 555                 560
Arg Asn Cys Met Asn Gln Asp Leu Ser Trp Lys Gly Pro Ala Lys Asn
                    565                 570                 575
Trp Glu Asn Val Leu Leu Gly Leu Gly Val Ala Gly Ser Ala Pro Gly
                580                 585                 590
Ile Glu Gly Asp Glu Ile Ala Pro Leu Ala Lys Glu Asn Val Ala Ala
            595                 600                 605
Pro
```

<210> SEQ ID NO 4
<211> LENGTH: 609
<212> TYPE: PRT
<213> ORGANISM: Artificial Sequence
<220> FEATURE:
<223> OTHER INFORMATION: Amino acid sequence of P168L+ T237A mutant GBSS1

<400> SEQUENCE: 4

```
Met Ser Ala Leu Thr Thr Ser Gln Leu Ala Thr Ser Ala Thr Gly Phe
1               5                   10                  15
Gly Ile Ala Asp Arg Ser Ala Pro Ser Ser Leu Leu Arg His Gly Phe
            20                  25                  30
Gln Gly Leu Lys Pro Arg Ser Pro Ala Gly Gly Asp Ala Thr Ser Leu
        35                  40                  45
Ser Val Thr Thr Ser Ala Arg Ala Thr Pro Lys Gln Gln Arg Ser Val
    50                  55                  60
Gln Arg Gly Ser Arg Arg Phe Pro Ser Val Val Val Tyr Ala Thr Gly
65                  70                  75                  80
Ala Gly Met Asn Val Val Phe Val Gly Ala Glu Met Ala Pro Trp Ser
                85                  90                  95
Lys Thr Gly Gly Leu Gly Asp Val Leu Gly Gly Leu Pro Pro Ala Met
            100                 105                 110
Ala Ala Asn Gly His Arg Val Met Val Ile Ser Pro Arg Tyr Asp Gln
        115                 120                 125
Tyr Lys Asp Ala Trp Asp Thr Ser Val Val Ala Glu Ile Lys Val Ala
    130                 135                 140
Asp Arg Tyr Glu Arg Val Arg Phe Phe His Cys Tyr Lys Arg Gly Val
145                 150                 155                 160
Asp Arg Val Phe Ile Asp His Leu Ser Phe Leu Glu Lys Val Trp Gly
                165                 170                 175
Lys Thr Gly Glu Lys Ile Tyr Gly Pro Asp Thr Gly Val Asp Tyr Lys
            180                 185                 190
Asp Asn Gln Met Arg Phe Ser Leu Leu Cys Gln Ala Ala Leu Glu Ala
        195                 200                 205
Pro Arg Ile Leu Asn Leu Asn Asn Asn Pro Tyr Phe Lys Gly Thr Tyr
    210                 215                 220
Gly Glu Asp Val Val Phe Val Cys Asn Asp Trp His Ala Gly Pro Leu
225                 230                 235                 240
Ala Ser Tyr Leu Lys Asn Asn Tyr Gln Pro Asn Gly Ile Tyr Arg Asn
                245                 250                 255
Ala Lys Val Ala Phe Cys Ile His Asn Ile Ser Tyr Gln Gly Arg Phe
            260                 265                 270
Ala Phe Glu Asp Tyr Pro Glu Leu Asn Leu Ser Glu Arg Phe Arg Ser
        275                 280                 285
Ser Phe Asp Phe Ile Asp Gly Tyr Asp Thr Pro Val Glu Gly Arg Lys
```

```
            290                 295                 300
Ile Asn Trp Met Lys Ala Gly Ile Leu Glu Ala Asp Arg Val Leu Thr
305                 310                 315                 320

Val Ser Pro Tyr Tyr Ala Glu Glu Leu Ile Ser Gly Ile Ala Arg Gly
                325                 330                 335

Cys Glu Leu Asp Asn Ile Met Arg Leu Thr Gly Ile Thr Gly Ile Val
                340                 345                 350

Asn Gly Met Asp Val Ser Glu Trp Asp Pro Ser Lys Asp Lys Tyr Ile
            355                 360                 365

Thr Ala Lys Tyr Asp Ala Thr Thr Ala Ile Glu Ala Lys Ala Leu Asn
        370                 375                 380

Lys Glu Ala Leu Gln Ala Glu Ala Gly Leu Pro Val Asp Arg Lys Ile
385                 390                 395                 400

Pro Leu Ile Ala Phe Ile Gly Arg Leu Glu Glu Gln Lys Gly Pro Asp
                405                 410                 415

Val Met Ala Ala Ala Ile Pro Glu Leu Met Gln Glu Asp Val Gln Ile
                420                 425                 430

Val Leu Leu Gly Thr Gly Lys Lys Lys Phe Glu Lys Leu Leu Lys Ser
            435                 440                 445

Met Glu Glu Lys Tyr Pro Gly Lys Val Arg Ala Val Val Lys Phe Asn
        450                 455                 460

Ala Pro Leu Ala His Leu Ile Met Ala Gly Ala Asp Val Leu Ala Val
465                 470                 475                 480

Pro Ser Arg Phe Glu Pro Cys Gly Leu Ile Gln Leu Gln Gly Met Arg
                485                 490                 495

Tyr Gly Thr Pro Cys Ala Cys Ala Ser Thr Gly Gly Leu Val Asp Thr
                500                 505                 510

Val Ile Glu Gly Lys Thr Gly Phe His Met Gly Arg Leu Ser Val Asp
            515                 520                 525

Cys Lys Val Val Glu Pro Ser Asp Val Lys Lys Val Ala Ala Thr Leu
        530                 535                 540

Lys Arg Ala Ile Lys Val Val Gly Thr Pro Ala Tyr Glu Glu Met Val
545                 550                 555                 560

Arg Asn Cys Met Asn Gln Asp Leu Ser Trp Lys Gly Pro Ala Lys Asn
                565                 570                 575

Trp Glu Asn Val Leu Leu Gly Leu Gly Val Ala Gly Ser Ala Pro Gly
                580                 585                 590

Ile Glu Gly Asp Glu Ile Ala Pro Leu Ala Lys Glu Asn Val Ala Ala
            595                 600                 605

Pro

<210> SEQ ID NO 5
<211> LENGTH: 1830
<212> TYPE: DNA
<213> ORGANISM: Artificial Sequence
<220> FEATURE:
<223> OTHER INFORMATION: Nucleic acid sequence of P168L mutant GBSS1

<400> SEQUENCE: 5
atgtcggctc tcaccacgtc ccagctcgcc acctcggcca ccggcttcgg catcgccgac      60
aggtcggcgc cgtcgtcgct gctccgccac gggttccagg gcctcaagcc ccgcagcccc     120
gccggcggcg acgcgacgtc gctcagcgtg acgaccagcg cgcgcgcgac gcccaagcag     180
cagcggtcgg tgcagcgtgg cagccggagg ttcccctccg tcgtcgtgta cgccaccggc     240
```

-continued

| | |
|---|---|
| gccggcatga acgtcgtgtt cgtcggcgcc gagatggccc cctggagcaa gaccggcggc | 300 |
| ctcggtgacg tcctcggtgg cctcccccct gccatggctg cgaatggcca cagggtcatg | 360 |
| gtgatctctc ctcggtacga ccagtacaag gacgcttggg ataccagcgt tgtggctgag | 420 |
| atcaaggttg cagacaggta cgagagggtg aggttttcc attgctacaa gcgtggagtc | 480 |
| gaccgtgtgt tcatcgacca tttgtcattc ctggagaagg tttggggaaa gaccggtgag | 540 |
| aagatctacg gacctgacac tggagttgat tacaaagaca accagatgcg tttcagcctt | 600 |
| ctttgccagg cagcactcga ggctcctagg atcctaaacc tcaacaacaa cccatacttc | 660 |
| aaaggaactt atggtgagga tgttgtgttc gtctgcaacg actggcacac tggcccactg | 720 |
| gcgagctacc tgaagaacaa ctaccagccc aatggcatct acaggaatgc aaaggttgct | 780 |
| ttctgcatcc acaacatctc ctaccagggc cgtttcgctt cgaggattta ccctgagctg | 840 |
| aacctctccg agaggttcag gtcatccttc gatttcatcg acgggtatga cacgccggtg | 900 |
| gagggcagga gatcaactg gatgaaggcc ggaatcctgg aagccgacag ggtgctcacc | 960 |
| gtgagcccgt actacgccga ggagctcatc tccggcatcg ccaggggatg cgagctcgac | 1020 |
| aacatcatgc ggctcaccgg catcaccggc atcgtcaacg gcatggacgt cagcgagtgg | 1080 |
| gatcctagca aggacaagta catcaccgcc aagtacgacg caaccacggc aatcgaggcg | 1140 |
| aaggcgctga acaaggaggc gttgcaggcg gaggcgggtc ttccggtcga caggaaaatc | 1200 |
| ccactgatcg cgttcatcgg caggctggag gaacagaagg ccctgacgt catggccgcc | 1260 |
| gccatcccgg agctcatgca ggaggacgtc cagatcgttc ttctgggtac tggaaagaag | 1320 |
| aagttcgaga agctgctcaa gagcatggag agaagtatc cgggcaaggt gagggccgtg | 1380 |
| gtgaagttca acgcgccgct tgctcatctc atcatggccg gagccgacgt gctcgccgtc | 1440 |
| cccagccgct tcgagccctg tggactcatc cagctgcagg ggatgagata cggaacgccc | 1500 |
| tgtgcttgcg cgtccaccgg tgggctcgtg gacacggtca tcgaaggcaa gactggtttc | 1560 |
| cacatgggcc gtctcagcgt cgactgcaag gtggtggagc caagcgacgt gaagaaggtg | 1620 |
| gcggccaccc tgaagcgcgc catcaaggtc gtcggcacgc cggcgtacga ggagatggtc | 1680 |
| aggaactgca tgaaccagga cctctcctgg aaggggcctg cgaagaactg ggagaatgtg | 1740 |
| ctcctgggcc tgggcgtcgc cggcagcgcg ccggggatcg aaggcgacga gatcgcgccg | 1800 |
| ctcgccaagg agaacgtggc tgctccttga | 1830 |

<210> SEQ ID NO 6
<211> LENGTH: 1830
<212> TYPE: DNA
<213> ORGANISM: Artificial Sequence
<220> FEATURE:
<223> OTHER INFORMATION: Nucleic acid sequence of T237A mutant GBSS1

<400> SEQUENCE: 6

| | |
|---|---|
| atgtcggctc tcaccacgtc ccagctcgcc acctcggcca ccggcttcgg catcgccgac | 60 |
| aggtcggcgc cgtcgtcgct gctccgccac gggttccagg gcctcaagcc ccgcagcccc | 120 |
| gccggcggcg acgcgacgtc gctcagcgtg acgaccagcg cgcgcgcgac gcccaagcag | 180 |
| cagcggtcgg tgcagcgtgg cagccggagg ttccctctcc gtcgtcgtgta cgccaccggc | 240 |
| gccggcatga acgtcgtgtt cgtcggcgcc gagatggccc cctggagcaa gaccggcggc | 300 |
| ctcggtgacg tcctcggtgg cctcccccct gccatggctg cgaatggcca cagggtcatg | 360 |
| gtgatctctc ctcggtacga ccagtacaag gacgcttggg ataccagcgt tgtggctgag | 420 |
| atcaaggttg cagacaggta cgagagggtg aggttttcc attgctacaa gcgtggagtc | 480 |

```
gaccgtgtgt tcatcgacca tccgtcattc ctggagaagg tttggggaaa gaccggtgag    540
aagatctacg gacctgacac tggagttgat tacaaagaca accagatgcg tttcagcctt    600
ctttgccagg cagcactcga ggctcctagg atcctaaacc tcaacaacaa cccatacttc    660
aaaggaactt atggtgagga tgttgtgttc gtctgcaacg actggcacgc tggcccactg    720
gcgagctacc tgaagaacaa ctaccagccc aatggcatct acaggaatgc aaaggttgct    780
ttctgcatcc acaacatctc ctaccagggc cgtttcgctt tcgaggatta ccctgagctg    840
aacctctccg agaggttcag gtcatccttc gatttcatcg acgggtatga cacgccggtg    900
gagggcagga agatcaactg gatgaaggcc ggaatcctgg aagccgacag ggtgctcacc    960
gtgagcccgt actacgccga ggagctcatc tccggcatcg ccagggatg cgagctcgac    1020 aacatcatgc ggctcaccgg catcaccggc atcgtcaacg gcatggacgt cagcgagtgg    1080
gatcctagca aggacaagta catcaccgcc aagtacgacg caaccacggc aatcgaggcg    1140
aaggcgctga acaaggaggc gttgcaggcg gaggcgggtc ttccggtcga caggaaaatc    1200
ccactgatcg cgttcatcgg caggctggag aacagaaagg gccctgacgt catggccgcc    1260
gccatcccgg agctcatgca ggaggacgtc cagatcgttc ttctgggtac tggaaagaag    1320
aagttcgaga agctgctcaa gagcatggag agaagtatc cgggcaaggt gagggccgtg    1380
gtgaagttca acgcgccgct tgctcatctc atcatggccg gagccgacgt gctcgccgtc    1440
cccagccgct tcgagccctg tggactcatc cagctgcagg ggatgagata cggaacgccc    1500
tgtgcttgcg cgtccaccgg tgggctcgtg gacacggtca tcgaaggcaa gactggtttc    1560
cacatgggcc gtctcagcgt cgactgcaag gtggtggagc caagcgacgt gaagaaggtg    1620
gcggccaccc tgaagcgcgc catcaaggtc gtcggcacgc cggcgtacga ggagatggtc    1680
aggaactgca tgaaccagga cctctcctgg aaggggcctg cgaagaactg ggagaatgtg    1740
ctcctgggcc tgggcgtcgc cggcagcgcg ccggggatcg aaggcgacga gatcgcgccg    1800
ctcgccaagg agaacgtggc tgctccttga                                    1830
```

<210> SEQ ID NO 7
<211> LENGTH: 1830
<212> TYPE: DNA
<213> ORGANISM: Artificial Sequence
<220> FEATURE:
<223> OTHER INFORMATION: Nucleic acid sequence of P168L+ T237A mutant
      GBSS1

<400> SEQUENCE: 7

```
atgtcggctc tcaccacgtc ccagctcgcc acctcggcca ccggcttcgg catcgccgac     60
aggtcggcgc cgtcgtcgct gctccgccac gggttccagg gcctcaagcc ccgcagcccc    120
gccggcggcg acgcgacgtc gctcagcgtg acgaccagcg cgcgcgcgac gcccaagcag    180
cagcggtcgg tgcagcgtgg cagccggagg ttcccctccg tcgtcgtgta cgccaccggc    240
gccggcatga acgtcgtgtt cgtcggcgcc gagatggccc cctggagcaa gaccggcggc    300
ctcggtgacg tcctcggtgg cctccccccct gccatggctg cgaatggcca cagggtcatg    360
gtgatctctc ctcggtacga ccagtacaag gacgcttggg ataccagcgt tgtggctgag    420
atcaaggttg cagacaggta cgagagggtg aggtttttcc attgctacaa gcgtggagtc    480
gaccgtgtgt tcatcgacca tttgtcattc ctggagaagg tttggggaaa gaccggtgag    540
aagatctacg gacctgacac tggagttgat tacaaagaca accagatgcg tttcagcctt    600
ctttgccagg cagcactcga ggctcctagg atcctaaacc tcaacaacaa cccatacttc    660
```

```
aaaggaactt atggtgagga tgttgtgttc gtctgcaacg actggcacgc tggcccactg    720
gcgagctacc tgaagaacaa ctaccagccc aatggcatct acaggaatgc aaaggttgct    780
ttctgcatcc acaacatctc ctaccagggc cgtttcgctt tcgaggatta ccctgagctg    840
aacctctccg agaggttcag gtcatccttc gatttcatcg acgggtatga cacgccggtg    900
gagggcagga agatcaactg gatgaaggcc ggaatcctgg aagccgacag ggtgctcacc    960
gtgagcccgt actacgccga ggagctcatc tccggcatcg ccaggggatg cgagctcgac   1020
aacatcatgc ggctcaccgg catcaccggc atcgtcaacg gcatggacgt cagcgagtgg   1080
gatcctagca aggacaagta catcaccgcc aagtacgacg caaccacggc aatcgaggcg   1140
aaggcgctga acaaggaggc gttgcaggcg gaggcgggtc ttccggtcga caggaaaatc   1200
ccactgatcg cgttcatcgg caggctggag gaacagaagg gccctgacgt catggccgcc   1260
gccatcccgg agctcatgca ggaggacgtc cagatcgttc ttctgggtac tggaaagaag   1320
aagttcgaga gctgctcaa gagcatggag agaagtatc cggcaaggt gagggccgtg   1380 gtgaagttca acgcgccgct gctcatctc atcatggccg gagccgacgt gctcgccgtc   1440
cccagccgct tcgagccctg tggactcatc agctgcagg ggatgagata cggaacgccc   1500
tgtgcttgcg cgtccaccgg tgggctcgtg gacacggtca tcgaaggcaa gactggtttc   1560
cacatgggcc gtctcagcgt cgactgcaag gtggtggagc aagcgacgt gaagaaggtg   1620 gcggccaccc tgaagcgcgc catcaaggtc gtcggcacgc cggcgtacga ggagatggtc   1680
aggaactgca tgaaccagga cctctcctgg aaggggcctg cgaagaactg ggagaatgtg   1740
ctcctgggcc tgggcgtcgc cggcagcgcg ccggggatcg aaggcgacga gatcgcgccg   1800
ctcgccaagg agaacgtggc tgctcccttga                                  1830

<210> SEQ ID NO 8
<211> LENGTH: 1830
<212> TYPE: DNA
<213> ORGANISM: Artificial Sequence
<220> FEATURE:
<223> OTHER INFORMATION: Nucleic acid sequence of Oryza sativa wild-type
      GBSS1

<400> SEQUENCE: 8
atgtcggctc tcaccacgtc ccagctcgcc acctcggcca ccggcttcgg catcgccgac     60
aggtcggcgc cgtcgtcgct gctccgccac gggttccagg cctcaagcc ccgcagcccc    120 gccggcggcg acgcgacgtc gctcagcgtg acgaccagcg cgcgcgcgac gcccaagcag    180
cagcggtcgg tgcagcgtgg cagccggagg ttcccctccg tcgtcgtgta cgccaccggc    240
gccggcatga acgtcgtgtt cgtcggcgcc gagatggccc cctggagcaa gaccggcggc    300
ctcggtgacg tcctcggtgg cctccccccct gccatggctg cgaatggcca cagggtcatg    360
gtgatctctc ctcggtacga ccagtacaag gacgcttggg ataccagcgt tgtggctgag    420
atcaaggttg cagacaggta cgagagggtg aggttttttcc attgctacaa gcgtggagtc    480
gaccgtgtgt tcatcgacca tccgtcattc ctggagaagg tttggggaaa gaccggtgag    540
aagatctacg acctgacac tggagttgat tacaagacaa accagatgcg tttcagcctt    600 cttgccagg cagcactcga ggtcctagg atcctaaacc tcaacaacaa cccatacttc    660
aaaggaactt atggtgagga tgttgtgttc gtctgcaacg actggcacac tggcccactg    720
gcgagctacc tgaagaacaa ctaccagccc aatggcatct acaggaatgc aaaggttgct    780
ttctgcatcc acaacatctc ctaccagggc cgtttcgctt tcgaggatta ccctgagctg    840
```

```
aacctctccg agaggttcag gtcatccttc gatttcatcg acgggtatga cacgccggtg      900
gagggcagga agatcaactg gatgaaggcc ggaatcctgg aagccgacag ggtgctcacc      960
gtgagcccgt actacgccga ggagctcatc tccggcatcg ccaggggatg cgagctcgac     1020
aacatcatgc ggctcaccgg catcaccggc atcgtcaacg gcatggacgt cagcgagtgg     1080
gatcctagca aggacaagta catcaccgcc aagtacgacg caaccacggc aatcgaggcg     1140
aaggcgctga acaaggaggc gttgcaggcg gaggcgggtc ttccggtcga caggaaaatc     1200
ccactgatcg cgttcatcgg caggctggag aacagaagg gccctgacgt catggccgcc      1260
gccatcccgg agctcatgca ggaggacgtc cagatcgttc ttctgggtac tggaaagaag     1320
aagttcgaga gctgctcaa gagcatggag agaagtatc cgggcaaggt gagggccgtg       1380
gtgaagttca acgcgccgct tgctcatctc atcatggccg gagccgacgt gctcgccgtc     1440
cccagccgct tcgagccctg tggactcatc cagctgcagg ggatgagata cggaacgccc     1500
tgtgcttgcg cgtccaccgg tgggctcgtg gacacggtca tcgaaggcaa gactggtttc     1560
cacatgggcc gtctcagcgt cgactgcaag gtggtggagc caagcgacgt gaagaaggtg     1620
gcggccaccc tgaagcgcgc catcaaggtc gtcggcacgc cggcgtacga ggagatggtc     1680
aggaactgca tgaaccagga cctctcctgg aaggggcctg cgaagaactg ggagaatgtg     1740
ctcctgggcc tgggcgtcgc cggcagcgcg ccggggatcg aaggcgacga gatcgcgccg     1800
ctcgccaagg agaacgtggc tgctccttga                                      1830
```

<210> SEQ ID NO 9
<211> LENGTH: 1830
<212> TYPE: DNA
<213> ORGANISM: Artificial Sequence
<220> FEATURE:
<223> OTHER INFORMATION: Nucleic acid sequence of L409L base mutation

<400> SEQUENCE: 9

```
atgtcggctc tcaccacgtc ccagctcgcc acctcggcca ccggcttcgg catcgccgac       60
aggtcggcgc cgtcgtcgct gctccgccac gggttccagg gcctcaagcc ccgcagcccc      120
gccggcggcg acgcgacgtc gctcagcgtg acgaccagcg cgcgcgcgac gcccaagcag      180
cagcggtcgg tgcagcgtgg cagccggagg ttccctccg tcgtcgtgta cgccaccggc       240
gccggcatga acgtcgtgtt cgtcggcgcc gagatggccc cctggagcaa gaccggcggc      300
ctcggtgacg tcctcggtgg cctccccct gccatggctg cgaatggcca cagggtcatg       360
gtgatctctc tcggtacgga ccagtacaag gacgcttggg ataccagcgt tgtggctgag      420
atcaaggttg cagacaggta cgagagggtg aggttttttcc attgctacaa gcgtggagtc     480
gaccgtgtgt tcatcgacca tccgtcattc ctggagaagg tttggggaaa gaccggtgag     540
aagatctacg acctgacac tggagttgat tacaaagaca accagatgcg tttcagcctt       600
ctttgccagg cagcactcga ggctcctagg atcctaaacc tcaacaacaa cccatacttc      660
aaaggaactt atggtgagga tgttgtgttc gtctgcaacg actggcacac tggcccactg      720
gcgagctacc tgaagaacaa ctaccagccc aatggcatct acaggaatgc aaaggttgct     780
ttctgcatcc acaacatctc ctaccaggggc cgtttcgctt cgaggattaa ccctgagctg      840
aacctctccg agaggttcag gtcatccttc gatttcatcg acgggtatga cacgccggtg     900
gagggcagga agatcaactg gatgaaggcc ggaatcctgg aagccgacag ggtgctcacc     960
gtgagcccgt actacgccga ggagctcatc tccggcatcg ccaggggatg cgagctcgac    1020
```

| | |
|---|---|
| aacatcatgc ggctcaccgg catcaccggc atcgtcaacg gcatggacgt cagcgagtgg | 1080 |
| gatcctagca aggacaagta catcaccgcc aagtacgacg caaccacggc aatcgaggcg | 1140 |
| aaggcgctga acaaggaggc gttgcaggcg gaggcgggtc ttccggtcga caggaaaatc | 1200 |
| ccactgatcg cgttcatcgg caggctagag aacagaagg gccctgacgt catggccgcc | 1260 |
| gccatcccgg agctcatgca ggaggacgtc cagatcgttc ttctgggtac tggaaagaag | 1320 |
| aagttcgaga agctgctcaa gagcatggag agaagtatc cggcaaggt gagggccgtg | 1380 |
| gtgaagttca acgcgccgct tgctcatctc atcatggccg agccgacgt gctcgccgtc | 1440 |
| cccagccgct tcgagccctg tggactcatc cagctgcagg ggatgagata cggaacgccc | 1500 |
| tgtgcttgcg cgtccaccgg tgggctcgtg gacacggtca tcgaaggcaa gactggtttc | 1560 |
| cacatgggcc gtctcagcgt cgactgcaag gtggtggagc caagcgacgt gaagaaggtg | 1620 |
| gcggccaccc tgaagcgcgc catcaaggtc gtcggcacgc cggcgtacga ggagatggtc | 1680 |
| aggaactgca tgaaccagga cctctcctgg aaggggcctg cgaagaactg ggagaatgtg | 1740 |
| ctcctgggcc tgggcgtcgc cggcagcgcg ccggggatcg aaggcgacga gatcgcgccg | 1800 |
| ctcgccaagg agaacgtggc tgctcccttga | 1830 |

<210> SEQ ID NO 10
<211> LENGTH: 1830
<212> TYPE: DNA
<213> ORGANISM: Artificial Sequence
<220> FEATURE:
<223> OTHER INFORMATION: Nucleic acid sequence of Q412Q base mutation

<400> SEQUENCE: 10

| | |
|---|---|
| atgtcggctc tcaccacgtc ccagctcgcc acctcggcca ccggcttcgg catcgccgac | 60 |
| aggtcggcgc cgtcgtcgct gctccgccac gggttccagg gcctcaagcc ccgcagcccc | 120 |
| gccggcggcg acgcgacgtc gctcagcgtg acgaccagcg cgcgcgcgac gcccaagcag | 180 |
| cagcggtcgt tgcagcgtgg cagcggagg ttcccctccg tcgtcgtgta cgccaccggc | 240 |
| gccggcatga acgtcgtgtt cgtcggcgcc gagatggccc cctggagcaa gaccggcggc | 300 |
| ctcggtgacg tcctcggtgg cctccccct gccatggctg cgaatggcca cagggtcatg | 360 |
| gtgatctctc ctcggtacga ccagtacaag gacgcttggg ataccagcgt tgtggctgag | 420 |
| atcaaggttg cagacaggta cgagagggtg aggttttttcc attgctacaa gcgtggagtc | 480 |
| gaccgtgtgt tcatcgacca tccgtcattc ctggagaagg tttggggaaa gaccggtgag | 540 |
| aagatctacg acctgacac tggagttgat tacaaagaca accagatgcg tttcagcctt | 600 |
| ctttgccagg cagcactcga ggctcctagg atcctaaacc tcaacaacaa cccatacttc | 660 |
| aaaggaactt atggtgagga tgttgtgttc gtctgcaacg actggcacac tgcccactg | 720 |
| gcgagctacc tgaagaacaa ctaccagccc aatggcatct acaggaatgc aaaggttgct | 780 |
| ttctgcatcc acaacatctc ctaccagggc cgtttcgctt cgaggattta cctgagctg | 840 |
| aacctctccg agaggttcag gtcatccttc gatttcatcg acgggtatga cacgccggtg | 900 |
| gagggcagga agatcaactg gatgaaggcc ggaatcctgg aagccgacag ggtgctcacc | 960 |
| gtgagcccgt actacgccga ggagctcatc tccggcatcg ccaggggatg cgagctcgac | 1020 |
| aacatcatgc ggctcaccgg catcaccggc atcgtcaacg gcatggacgt cagcgagtgg | 1080 |
| gatcctagca aggacaagta catcaccgcc aagtacgacg caaccacggc aatcgaggcg | 1140 |
| aaggcgctga acaaggaggc gttgcaggcg gaggcgggtc ttccggtcga caggaaaatc | 1200 |
| ccactgatcg cgttcatcgg caggctggag gaacaaaagg gccctgacgt catggccgcc | 1260 |

-continued

```
gccatcccgg agctcatgca ggaggacgtc cagatcgttc ttctgggtac tggaaagaag      1320
aagttcgaga agctgctcaa gagcatggag gagaagtatc cgggcaaggt gagggccgtg      1380
gtgaagttca acgcgccgct tgctcatctc atcatggccg gagccgacgt gctcgccgtc      1440
cccagccgct tcgagccctg tggactcatc cagctgcagg ggatgagata cggaacgccc      1500
tgtgcttgcg cgtccaccgg tgggctcgtg gacacggtca tcgaaggcaa gactggtttc      1560
cacatgggcc gtctcagcgt cgactgcaag gtggtggagc caagcgacgt gaagaaggtg      1620
gcggccaccc tgaagcgcgc catcaaggtc gtcggcacgc cggcgtacga ggagatggtc      1680
aggaactgca tgaaccagga cctctcctgg aaggggcctg cgaagaactg ggagaatgtg      1740
ctcctgggcc tgggcgtcgc cggcagcgcg ccggggatcg aaggcgacga gatcgcgccg      1800
ctcgccaagg agaacgtggc tgctccttga                                      1830
```

<210> SEQ ID NO 11
<211> LENGTH: 1830
<212> TYPE: DNA
<213> ORGANISM: Artificial Sequence
<220> FEATURE:
<223> OTHER INFORMATION: Nucleic acid sequence of E410E base mutation

<400> SEQUENCE: 11

```
atgtcggctc tcaccacgtc ccagctcgcc acctcggcca ccggcttcgg catcgccgac        60
aggtcggcgc cgtcgtcgct gctccgccac gggttccagg gcctcaagcc ccgcagcccc       120
gccggcggcg acgcgacgtc gctcagcgtg acgaccagcg cgcgcgcgac gcccaagcag       180
cagcggtcgg tgcagcgtgg cagccggagg ttcccctccg tcgtcgtgta cgccaccggc       240
gccggcatga acgtcgtgtt cgtcggcgcc gagatggccc cctggagcaa gaccggcggc       300
ctcggtgacg tcctcggtgg cctccccccct gccatggctg cgaatggcca cagggtcatg       360
gtgatctctc ctcggtacga ccagtacaag gacgcttggg ataccagcgt tgtggctgag       420
atcaaggttg cagacaggta cgagagggtg aggttttttcc attgctacaa gcgtggagtc       480
gaccgtgtgt tcatcgacca tccgtcattc ctggagaagg tttggggaaa gaccggtgag       540
aagatctacg gacctgacac tggagttgat tacaaagaca accagatgcg tttcagcctt       600
ctttgccagg cagcactcga ggctcctagg atcctaaacc tcaacaacaa cccatacttc       660
aaaggaactt atggtgagga tgttgtgttc gtctgcaacg actggcacac tggcccactg       720
gcgagctacc tgaagaacaa ctaccagccc aatggcatct acaggaatgc aaaggttgct       780
ttctgcatcc acaacatctc ctaccagggc cgtttcgctt cgaggattaa ccctgagctg       840
aacctctccg agaggttcag gtcatccttc gatttcatcg acgggtatga cacgccggtg       900
gagggcagga agatcaactg gatgaaggcc ggaatcctgg aagccgacag ggtgctcacc       960
gtgagcccgt actacgccga ggagctcatc tccggcatcg ccaggggatg cgagctcgac      1020
aacatcatgc ggctcaccgg catcaccggc atcgtcaacg gcatggacgt cagcgagtgg      1080
gatcctagca aggacaagta catcaccgcc aagtacgacg caaccacggc aatcgaggcg      1140
aaggcgctga acaaggaggc gttgcaggcg gaggcgggtc ttccggtcga caggaaaatc      1200
ccactgatcg cgttcatcgg caggctggaa gaacagaagg gccctgacgt catggccgcc      1260
gccatcccgg agctcatgca ggaggacgtc cagatcgttc ttctgggtac tggaaagaag      1320
aagttcgaga agctgctcaa gagcatggag gagaagtatc cgggcaaggt gagggccgtg      1380
gtgaagttca acgcgccgct tgctcatctc atcatggccg gagccgacgt gctcgccgtc      1440
```

```
cccagccgct tcgagccctg tggactcatc cagctgcagg ggatgagata cggaacgccc    1500
tgtgcttgcg cgtccaccgg tgggctcgtg gacacggtca tcgaaggcaa gactggtttc    1560
cacatgggcc gtctcagcgt cgactgcaag gtggtggagc caagcgacgt gaagaaggtg    1620
gcggccaccc tgaagcgcgc catcaaggtc gtcggcacgc cggcgtacga ggagatggtc    1680
aggaactgca tgaaccagga cctctcctgg aaggggcctg cgaagaactg ggagaatgtg    1740
ctcctgggcc tgggcgtcgc cggcagcgcg ccggggatcg aaggcgacga gatcgcgccg    1800
ctcgccaagg agaacgtggc tgctcccttga                                    1830
```

<210> SEQ ID NO 12
<211> LENGTH: 1830
<212> TYPE: DNA
<213> ORGANISM: Artificial Sequence
<220> FEATURE:
<223> OTHER INFORMATION: Nucleic acid sequence of E411K base mutation

<400> SEQUENCE: 12

```
atgtcggctc tcaccacgtc ccagctcgcc acctcggcca ccggcttcgg catcgccgac     60
aggtcggcgc cgtcgtcgct gctccgccac gggttccagg gcctcaagcc ccgcagcccc    120
gccggcggcg acgcgacgtc gctcagcgtg acgaccagcg cgcgcgcgac gcccaagcag    180
cagcggtcgg tgcagcgtgg cagccggagg ttcccctccg tcgtcgtgta cgccaccggc    240
gccggcatga acgtcgtgtt cgtcggcgcc gagatggccc cctggagcaa gaccggcggc    300
ctcggtgacg tcctcggtgg cctccccccct gccatggctg cgaatggcca cagggtcatg    360
gtgatctctc ctcggtacga ccagtacaag gacgcttggg ataccagcgt tgtggctgag    420
atcaaggttg cagacaggta cgagagggtg aggtttttcc attgctacaa gcgtggagtc    480
gaccgtgtgt tcatcgacca tccgtcattc ctggagaagg tttggggaaa gaccggtgag    540
aagatctacg gacctgacac tggagttgat tacaaagaca accagatgcg tttcagcctt    600 cttttgccagg cagcactcga ggctcctagg atcctaaacc tcaacaacaa cccatacttc    660
aaaggaactt atggtgagga tgttgtgttc gtctgcaacg actggcacac tggcccactg    720
gcgagctacc tgaagaacaa ctaccagccc aatggcatct acaggaatgc aaaggttgct    780
ttctgcatcc acaacatctc ctaccagggc cgtttcgctt tcgaggatta ccctgagctg    840
aacctctccg agaggttcag gtcatccttc gatttcatcg acgggtatga cacgccggtg    900
gagggcagga agatcaactg gatgaaggcc ggaatcctgg aagccgacag ggtgctcacc    960
gtgagcccgt actacgccga ggagctcatc tccggcatcg ccaggggatg cgagctcgac   1020
aacatcatgc ggctcaccgg catcaccggc atcgtcaacg gcatggacgt cagcgagtgg   1080
gatcctagca aggacaagta catcaccgcc aagtacgacg caaccacggc aatcgaggcg   1140
aaggcgctga caaggaggc gttgcaggcg gaggcgggtc ttccggtcga caggaaaatc   1200
ccactgatcg cgttcatcgg caggctggag aaacagaagg ccctgacgt catggccgcc   1260 gccatcccgg agctcatgca ggaggacgtc cagatcgttc ttctgggtac tggaaagaag   1320
aagttcgaga gctgctcaa gagcatggag gagaagtatc cggcaaggt gagggccgtg   1380 gtgaagttca cgcgccgct tgctcatctc atcatggccg gagccgacgt gctcgccgtc   1440
cccagccgct tcgagccctg tggactcatc cagctgcagg ggatgagata cggaacgccc   1500
tgtgcttgcg cgtccaccgg tgggctcgtg gacacggtca tcgaaggcaa gactggtttc   1560
cacatgggcc gtctcagcgt cgactgcaag gtggtggagc caagcgacgt gaagaaggtg   1620
gcggccaccc tgaagcgcgc catcaaggtc gtcggcacgc cggcgtacga ggagatggtc   1680
```

-continued

```
aggaactgca tgaaccagga cctctcctgg aagggcctg cgaagaactg ggagaatgtg    1740
ctcctgggcc tgggcgtcgc cggcagcgcg ccggggatcg aaggcgacga gatcgcgccg    1800
ctcgccaagg agaacgtggc tgctccttga                                     1830
```

<210> SEQ ID NO 13
<211> LENGTH: 609
<212> TYPE: PRT
<213> ORGANISM: Artificial Sequence
<220> FEATURE:
<223> OTHER INFORMATION: Amino acid sequence of Q427R mutant GBSS1

<400> SEQUENCE: 13

```
Met Ser Ala Leu Thr Thr Ser Gln Leu Ala Thr Ser Ala Thr Gly Phe
1               5                   10                  15

Gly Ile Ala Asp Arg Ser Ala Pro Ser Ser Leu Leu Arg His Gly Phe
                20                  25                  30

Gln Gly Leu Lys Pro Arg Ser Pro Ala Gly Gly Asp Ala Thr Ser Leu
            35                  40                  45

Ser Val Thr Thr Ser Ala Arg Ala Thr Pro Lys Gln Gln Arg Ser Val
    50                  55                  60

Gln Arg Gly Ser Arg Arg Phe Pro Ser Val Val Tyr Ala Thr Gly
65                  70                  75                  80

Ala Gly Met Asn Val Val Phe Val Gly Ala Glu Met Ala Pro Trp Ser
                85                  90                  95

Lys Thr Gly Gly Leu Gly Asp Val Leu Gly Gly Leu Pro Pro Ala Met
            100                 105                 110

Ala Ala Asn Gly His Arg Val Met Val Ile Ser Pro Arg Tyr Asp Gln
        115                 120                 125

Tyr Lys Asp Ala Trp Asp Thr Ser Val Val Ala Glu Ile Lys Val Ala
    130                 135                 140

Asp Arg Tyr Glu Arg Val Arg Phe Phe His Cys Tyr Lys Arg Gly Val
145                 150                 155                 160

Asp Arg Val Phe Ile Asp His Pro Ser Phe Leu Glu Lys Val Trp Gly
                165                 170                 175

Lys Thr Gly Glu Lys Ile Tyr Gly Pro Asp Thr Gly Val Asp Tyr Lys
            180                 185                 190

Asp Asn Gln Met Arg Phe Ser Leu Leu Cys Gln Ala Ala Leu Glu Ala
        195                 200                 205

Pro Arg Ile Leu Asn Leu Asn Asn Asn Pro Tyr Phe Lys Gly Thr Tyr
    210                 215                 220

Gly Glu Asp Val Val Phe Val Cys Asn Asp Trp His Thr Gly Pro Leu
225                 230                 235                 240

Ala Ser Tyr Leu Lys Asn Asn Tyr Gln Pro Asn Gly Ile Tyr Arg Asn
                245                 250                 255

Ala Lys Val Ala Phe Cys Ile His Asn Ile Ser Tyr Gln Gly Arg Phe
            260                 265                 270

Ala Phe Glu Asp Tyr Pro Glu Leu Asn Leu Ser Glu Arg Phe Arg Ser
        275                 280                 285

Ser Phe Asp Phe Ile Asp Gly Tyr Asp Thr Pro Val Glu Gly Arg Lys
    290                 295                 300

Ile Asn Trp Met Lys Ala Gly Ile Leu Glu Ala Asp Arg Val Leu Thr
305                 310                 315                 320

Val Ser Pro Tyr Tyr Ala Glu Glu Leu Ile Ser Gly Ile Ala Arg Gly
                325                 330                 335
```

```
Cys Glu Leu Asp Asn Ile Met Arg Leu Thr Gly Ile Thr Gly Ile Val
            340                 345                 350

Asn Gly Met Asp Val Ser Glu Trp Asp Pro Ser Lys Asp Lys Tyr Ile
            355                 360                 365

Thr Ala Lys Tyr Asp Ala Thr Thr Ala Ile Glu Ala Lys Ala Leu Asn
        370                 375                 380

Lys Glu Ala Leu Gln Ala Glu Ala Gly Leu Pro Val Asp Arg Lys Ile
385                 390                 395                 400

Pro Leu Ile Ala Phe Ile Gly Arg Leu Glu Glu Gln Lys Gly Pro Asp
                405                 410                 415

Val Met Ala Ala Ala Ile Pro Glu Leu Met Arg Glu Asp Val Gln Ile
            420                 425                 430

Val Leu Leu Gly Thr Gly Lys Lys Lys Phe Glu Lys Leu Leu Lys Ser
            435                 440                 445

Met Glu Glu Lys Tyr Pro Gly Lys Val Arg Ala Val Val Lys Phe Asn
        450                 455                 460

Ala Pro Leu Ala His Leu Ile Met Ala Gly Ala Asp Val Leu Ala Val
465                 470                 475                 480

Pro Ser Arg Phe Glu Pro Cys Gly Leu Ile Gln Leu Gln Gly Met Arg
                485                 490                 495

Tyr Gly Thr Pro Cys Ala Cys Ala Ser Thr Gly Gly Leu Val Asp Thr
            500                 505                 510

Val Ile Glu Gly Lys Thr Gly Phe His Met Gly Arg Leu Ser Val Asp
            515                 520                 525

Cys Lys Val Val Glu Pro Ser Asp Val Lys Lys Val Ala Ala Thr Leu
        530                 535                 540

Lys Arg Ala Ile Lys Val Val Gly Thr Pro Ala Tyr Glu Glu Met Val
545                 550                 555                 560

Arg Asn Cys Met Asn Gln Asp Leu Ser Trp Lys Gly Pro Ala Lys Asn
                565                 570                 575

Trp Glu Asn Val Leu Leu Gly Leu Gly Val Ala Gly Ser Ala Pro Gly
            580                 585                 590

Ile Glu Gly Asp Glu Ile Ala Pro Leu Ala Lys Glu Asn Val Ala Ala
            595                 600                 605

Pro

<210> SEQ ID NO 14
<211> LENGTH: 609
<212> TYPE: PRT
<213> ORGANISM: Artificial Sequence
<220> FEATURE:
<223> OTHER INFORMATION: Amino acid sequence of E428G mutant GBSS1

<400> SEQUENCE: 14

Met Ser Ala Leu Thr Thr Ser Gln Leu Ala Thr Ser Ala Thr Gly Phe
1               5                   10                  15

Gly Ile Ala Asp Arg Ser Ala Pro Ser Ser Leu Leu Arg His Gly Phe
            20                  25                  30

Gln Gly Leu Lys Pro Arg Ser Pro Ala Gly Gly Asp Ala Thr Ser Leu
        35                  40                  45

Ser Val Thr Thr Ser Ala Arg Ala Thr Pro Lys Gln Gln Arg Ser Val
    50                  55                  60

Gln Arg Gly Ser Arg Arg Phe Pro Ser Val Val Val Tyr Ala Thr Gly
65                  70                  75                  80
```

-continued

```
Ala Gly Met Asn Val Phe Val Gly Ala Glu Met Ala Pro Trp Ser
                 85                  90                  95
Lys Thr Gly Gly Leu Gly Asp Val Leu Gly Gly Leu Pro Pro Ala Met
            100                 105                 110
Ala Ala Asn Gly His Arg Val Met Val Ile Ser Pro Arg Tyr Asp Gln
        115                 120                 125
Tyr Lys Asp Ala Trp Asp Thr Ser Val Val Ala Glu Ile Lys Val Ala
    130                 135                 140
Asp Arg Tyr Glu Arg Val Arg Phe Phe His Cys Tyr Lys Arg Gly Val
145                 150                 155                 160
Asp Arg Val Phe Ile Asp His Pro Ser Phe Leu Glu Lys Val Trp Gly
                165                 170                 175
Lys Thr Gly Glu Lys Ile Tyr Gly Pro Asp Thr Gly Val Asp Tyr Lys
            180                 185                 190
Asp Asn Gln Met Arg Phe Ser Leu Leu Cys Gln Ala Ala Leu Glu Ala
        195                 200                 205
Pro Arg Ile Leu Asn Leu Asn Asn Asn Pro Tyr Phe Lys Gly Thr Tyr
    210                 215                 220
Gly Glu Asp Val Val Phe Val Cys Asn Asp Trp His Thr Gly Pro Leu
225                 230                 235                 240
Ala Ser Tyr Leu Lys Asn Asn Tyr Gln Pro Asn Gly Ile Tyr Arg Asn
                245                 250                 255
Ala Lys Val Ala Phe Cys Ile His Asn Ile Ser Tyr Gln Gly Arg Phe
            260                 265                 270
Ala Phe Glu Asp Tyr Pro Glu Leu Asn Leu Ser Glu Arg Phe Arg Ser
        275                 280                 285
Ser Phe Asp Phe Ile Asp Gly Tyr Asp Thr Pro Val Glu Gly Arg Lys
    290                 295                 300
Ile Asn Trp Met Lys Ala Gly Ile Leu Glu Ala Asp Arg Val Leu Thr
305                 310                 315                 320
Val Ser Pro Tyr Tyr Ala Glu Glu Leu Ile Ser Gly Ile Ala Arg Gly
                325                 330                 335
Cys Glu Leu Asp Asn Ile Met Arg Leu Thr Gly Ile Thr Gly Ile Val
            340                 345                 350
Asn Gly Met Asp Val Ser Glu Trp Asp Pro Ser Lys Asp Lys Tyr Ile
        355                 360                 365
Thr Ala Lys Tyr Asp Ala Thr Thr Ala Ile Glu Ala Lys Ala Leu Asn
    370                 375                 380
Lys Glu Ala Leu Gln Ala Glu Ala Gly Leu Pro Val Asp Arg Lys Ile
385                 390                 395                 400
Pro Leu Ile Ala Phe Ile Gly Arg Leu Glu Glu Gln Lys Gly Pro Asp
                405                 410                 415
Val Met Ala Ala Ala Ile Pro Glu Leu Met Gln Gly Asp Val Gln Ile
            420                 425                 430
Val Leu Leu Gly Thr Gly Lys Lys Lys Phe Glu Lys Leu Leu Lys Ser
        435                 440                 445
Met Glu Glu Lys Tyr Pro Gly Lys Val Arg Ala Val Val Lys Phe Asn
    450                 455                 460
Ala Pro Leu Ala His Leu Ile Met Ala Gly Ala Asp Val Leu Ala Val
465                 470                 475                 480
Pro Ser Arg Phe Glu Pro Cys Gly Leu Ile Gln Leu Gln Gly Met Arg
                485                 490                 495
Tyr Gly Thr Pro Cys Ala Cys Ala Ser Thr Gly Gly Leu Val Asp Thr
```

-continued

```
                500                 505                 510
Val Ile Glu Gly Lys Thr Gly Phe His Met Gly Arg Leu Ser Val Asp
            515                 520                 525

Cys Lys Val Val Glu Pro Ser Asp Val Lys Val Ala Ala Thr Leu
        530                 535                 540

Lys Arg Ala Ile Lys Val Val Gly Thr Pro Ala Tyr Glu Glu Met Val
545                 550                 555                 560

Arg Asn Cys Met Asn Gln Asp Leu Ser Trp Lys Gly Pro Ala Lys Asn
                565                 570                 575

Trp Glu Asn Val Leu Leu Gly Leu Gly Val Ala Gly Ser Ala Pro Gly
            580                 585                 590

Ile Glu Gly Asp Glu Ile Ala Pro Leu Ala Lys Glu Asn Val Ala Ala
        595                 600                 605

Pro
```

<210> SEQ ID NO 15
<211> LENGTH: 609
<212> TYPE: PRT
<213> ORGANISM: Artificial Sequence
<220> FEATURE:
<223> OTHER INFORMATION: Amino acid sequence of Q427R + E428G mutant
      GBSS1

<400> SEQUENCE: 15

```
Met Ser Ala Leu Thr Thr Ser Gln Leu Ala Thr Ser Ala Thr Gly Phe
1               5                   10                  15

Gly Ile Ala Asp Arg Ser Ala Pro Ser Ser Leu Leu Arg His Gly Phe
            20                  25                  30

Gln Gly Leu Lys Pro Arg Ser Pro Ala Gly Gly Asp Ala Thr Ser Leu
        35                  40                  45

Ser Val Thr Thr Ser Ala Arg Ala Thr Pro Lys Gln Gln Arg Ser Val
    50                  55                  60

Gln Arg Gly Ser Arg Arg Phe Pro Ser Val Val Val Tyr Ala Thr Gly
65                  70                  75                  80

Ala Gly Met Asn Val Val Phe Val Gly Ala Glu Met Ala Pro Trp Ser
                85                  90                  95

Lys Thr Gly Gly Leu Gly Asp Val Leu Gly Gly Leu Pro Pro Ala Met
            100                 105                 110

Ala Ala Asn Gly His Arg Val Met Val Ile Ser Pro Arg Tyr Asp Gln
        115                 120                 125

Tyr Lys Asp Ala Trp Asp Thr Ser Val Val Ala Glu Ile Lys Val Ala
    130                 135                 140

Asp Arg Tyr Glu Arg Val Arg Phe Phe His Cys Tyr Lys Arg Gly Val
145                 150                 155                 160

Asp Arg Val Phe Ile Asp His Pro Ser Phe Leu Glu Lys Val Trp Gly
                165                 170                 175

Lys Thr Gly Glu Lys Ile Tyr Gly Pro Asp Thr Gly Val Asp Tyr Lys
            180                 185                 190

Asp Asn Gln Met Arg Phe Ser Leu Leu Cys Gln Ala Ala Leu Glu Ala
        195                 200                 205

Pro Arg Ile Leu Asn Leu Asn Asn Asn Pro Tyr Phe Lys Gly Thr Tyr
    210                 215                 220

Gly Glu Asp Val Val Phe Val Cys Asn Asp Trp His Thr Gly Pro Leu
225                 230                 235                 240

Ala Ser Tyr Leu Lys Asn Asn Tyr Gln Pro Asn Gly Ile Tyr Arg Asn
```

-continued

```
                    245                 250                 255
Ala Lys Val Ala Phe Cys Ile His Asn Ile Ser Tyr Gln Gly Arg Phe
                260                 265                 270

Ala Phe Glu Asp Tyr Pro Glu Leu Asn Leu Ser Glu Arg Phe Arg Ser
            275                 280                 285

Ser Phe Asp Phe Ile Asp Gly Tyr Asp Thr Pro Val Glu Gly Arg Lys
        290                 295                 300

Ile Asn Trp Met Lys Ala Gly Ile Leu Glu Ala Asp Arg Val Leu Thr
305                 310                 315                 320

Val Ser Pro Tyr Tyr Ala Glu Glu Leu Ile Ser Gly Ile Ala Arg Gly
                325                 330                 335

Cys Glu Leu Asp Asn Ile Met Arg Leu Thr Gly Ile Thr Gly Ile Val
                340                 345                 350

Asn Gly Met Asp Val Ser Glu Trp Asp Pro Ser Lys Asp Lys Tyr Ile
            355                 360                 365

Thr Ala Lys Tyr Asp Ala Thr Thr Ala Ile Glu Ala Lys Ala Leu Asn
        370                 375                 380

Lys Glu Ala Leu Gln Ala Glu Ala Gly Leu Pro Val Asp Arg Lys Ile
385                 390                 395                 400

Pro Leu Ile Ala Phe Ile Gly Arg Leu Glu Glu Gln Lys Gly Pro Asp
                405                 410                 415

Val Met Ala Ala Ala Ile Pro Glu Leu Met Arg Gly Asp Val Gln Ile
                420                 425                 430

Val Leu Leu Gly Thr Gly Lys Lys Lys Phe Glu Lys Leu Leu Lys Ser
            435                 440                 445

Met Glu Glu Lys Tyr Pro Gly Lys Val Arg Ala Val Val Lys Phe Asn
    450                 455                 460

Ala Pro Leu Ala His Leu Ile Met Ala Gly Ala Asp Val Leu Ala Val
465                 470                 475                 480

Pro Ser Arg Phe Glu Pro Cys Gly Leu Ile Gln Leu Gln Gly Met Arg
                485                 490                 495

Tyr Gly Thr Pro Cys Ala Cys Ala Ser Thr Gly Gly Leu Val Asp Thr
            500                 505                 510

Val Ile Glu Gly Lys Thr Gly Phe His Met Gly Arg Leu Ser Val Asp
        515                 520                 525

Cys Lys Val Val Glu Pro Ser Asp Val Lys Lys Val Ala Ala Thr Leu
530                 535                 540

Lys Arg Ala Ile Lys Val Val Gly Thr Pro Ala Tyr Glu Glu Met Val
545                 550                 555                 560

Arg Asn Cys Met Asn Gln Asp Leu Ser Trp Lys Gly Pro Ala Lys Asn
                565                 570                 575

Trp Glu Asn Val Leu Leu Gly Leu Gly Val Ala Gly Ser Ala Pro Gly
                580                 585                 590

Ile Glu Gly Asp Glu Ile Ala Pro Leu Ala Lys Glu Asn Val Ala Ala
            595                 600                 605

Pro
```

<210> SEQ ID NO 16
<211> LENGTH: 1830
<212> TYPE: DNA
<213> ORGANISM: Artificial Sequence
<220> FEATURE:
<223> OTHER INFORMATION: Nucleic acid sequence of Q427R mutant GBSS1

<400> SEQUENCE: 16

```
atgtcggctc tcaccacgtc ccagctcgcc acctcggcca ccggcttcgg catcgccgac    60
aggtcggcgc cgtcgtcgct gctccgccac gggttccagg gcctcaagcc ccgcagcccc   120
gccggcggcg acgcgacgtc gctcagcgtg acgaccagcg cgcgcgcgac gcccaagcag   180
cagcggtcgg tgcagcgtgg cagccggagg ttcccctccg tcgtcgtgta cgccaccggc   240
gccggcatga acgtcgtgtt cgtcggcgcc gagatggccc cctggagcaa gaccggcggc   300
ctcggtgacg tcctcggtgg cctccccccct gccatggctg cgaatggcca cagggtcatg   360
gtgatctctc ctcggtacga ccagtacaag gacgcttggg ataccagcgt tgtggctgag   420
atcaaggttg cagacaggta cgagagggtg aggttttttcc attgctacaa gcgtggagtc   480
gaccgtgtgt tcatcgacca tccgtcattc ctggagaagg tttggggaaa gaccggtgag   540
aagatctacg acctgacac tggagttgat tacaaagaca accagatgcg tttcagcctt   600
ctttgccagg cagcactcga ggctcctagg atcctaaacc tcaacaacaa cccatacttc   660
aaaggaactt atggtgagga tgttgtgttc gtctgcaacg actggcacac tggcccactg   720
gcgagctacc tgaagaacaa ctaccagccc aatggcatct acaggaatgc aaaggttgct   780
ttctgcatcc acaacatctc ctaccagggc cgtttcgctt tcgaggatta ccctgagctg   840
aacctctccg agaggttcag gtcatccttc gatttcatcg acgggtatga cacgccggtg   900
gagggcagga agatcaactg gatgaaggcc ggaatcctgg aagccgacag ggtgctcacc   960
gtgagcccgt actacgccga ggagctcatc tccggcatcg ccaggggatg cgagctcgac  1020
aacatcatgc ggctcaccgg catcaccgga atcgtcaacg gcatggacgt cagcgagtgg  1080
gatcctagca aggacaagta catcaccgcc aagtacgacg caaccacggc aatcgaggcg  1140
aaggcgctga acaaggaggc gttgcaggcg gaggcgggtc ttccggtcga caggaaaatc  1200
ccactgatcg cgttcatcgg caggctggag gaacagaagg gccctgacgt catggccgcc  1260
gccatcccgg agctcatgcg ggaggacgtc cagatcgttc ttctgggtac tggaaagaag  1320
aagttcgaga agctgctcaa gagcatggag agaagtatc cgggcaaggt gagggccgtg  1380
gtgaagttca cgcgccgct tgctcatctc atcatggccg gagccgacgt gctcgccgtc  1440
cccagccgct tcgagccctg tggactcatc cagctgcagg ggatgagata cggaacgccc  1500
tgtgcttgcg cgtccaccgg tgggctcgtg gacacggtca tcgaaggcaa gactggtttc  1560
cacatgggcc gtctcagcgt cgactgcaag gtggtggagc caagcgacgt gaagaaggtg  1620
gcggccaccc tgaagcgcgc catcaaggtc gtcggcacgc cggcgtacga ggagatggtc  1680
aggaactgca tgaaccagga cctctcctgg aaggggcctg cgaagaactg ggagaatgtg  1740
ctcctgggcc tgggcgtcgc cggcagcgcg ccgggggatcg aaggcgacga gatcgcgccg  1800
ctcgccaagg agaacgtggc tgctccttga                                    1830
```

<210> SEQ ID NO 17
<211> LENGTH: 1830
<212> TYPE: DNA
<213> ORGANISM: Artificial Sequence
<220> FEATURE:
<223> OTHER INFORMATION: Nucleic acid sequence of E428G mutant GBSS1

<400> SEQUENCE: 17

```
atgtcggctc tcaccacgtc ccagctcgcc acctcggcca ccggcttcgg catcgccgac    60
aggtcggcgc cgtcgtcgct gctccgccac gggttccagg gcctcaagcc ccgcagcccc   120
gccggcggcg acgcgacgtc gctcagcgtg acgaccagcg cgcgcgcgac gcccaagcag   180
```

-continued

```
cagcggtcgg tgcagcgtgg cagccggagg ttcccctccg tcgtcgtgta cgccaccggc      240
gccggcatga acgtcgtgtt cgtcggcgcc gagatggccc cctggagcaa gaccggcggc      300
ctcggtgacg tcctcggtgg cctcccccct gccatggctg cgaatggcca cagggtcatg      360
gtgatctctc ctcggtacga ccagtacaag gacgcttggg ataccagcgt tgtggctgag      420
atcaaggttg cagacaggta cgagagggtg aggttttttcc attgctacaa gcgtggagtc      480
gaccgtgtgt tcatcgacca tccgtcattc ctggagaagg tttggggaaa gaccggtgag      540
aagatctacg gacctgacac tggagttgat tacaaagaca ccagatgcg tttcagcctt      600 ctttgccagg cagcactcga ggctcctagg atcctaaacc tcaacaacaa cccatacttc      660
aaaggaactt atggtgagga tgttgtgttc gtctgcaacg actggcacac tggcccactg      720
gcgagctacc tgaagaacaa ctaccagccc aatggcatct acaggaatgc aaaggttgct      780
ttctgcatcc acaacatctc ctaccagggc cgtttcgctt tcgaggatta ccctgagctg      840
aacctctccg agaggttcag gtcatccttc gatttcatcg acgggtatga cacgccggtg      900
gagggcagga agatcaactg gatgaaggcc ggaatcctgg aagccgacag ggtgctcacc      960
gtgagcccgt actacgccga ggagctcatc tccggcatcg ccaggggatg cgagctcgac     1020
aacatcatgc ggctcaccgg catcaccggc atcgtcaacg gcatggacgt cagcgagtgg     1080
gatcctagca aggacaagta catcaccgcc aagtacgacg caaccacggc aatcgaggcg     1140
aaggcgctga acaaggaggc gttgcaggcg gaggcgggtc ttccggtcga caggaaaatc     1200
ccactgatcg cgttcatcgg caggctggag gaacagaagg gccctgacgt catggccgcc     1260
gccatcccgg agctcatgca gggggacgtc cagatcgttc ttctgggtac tggaaagaag     1320
aagttcgaga gctgctcaa gagcatggag gagaagtatc cgggcaaggt gagggccgtg     1380
gtgaagttca acgcgccgct tgctcatctc atcatggccg gagccgacgt gctcgccgtc     1440
cccagccgct tcgagccctg tggactcatc cagctgcagg ggatgagata cggaacgccc     1500
tgtgcttgcg cgtccaccgg tgggctcgtg acacggtca tcgaaggcaa gactggtttc     1560
cacatgggcc gtctcagcgt cgactgcaag gtggtggagc caagcgacgt gaagaaggtg     1620
gcggccaccc tgaagcgcgc catcaaggtc gtcggcacgc cggcgtacga ggagatggtc     1680
aggaactgca tgaaccagga cctctcctgg aagggcctg cgaagaactg ggagaatgtg     1740
ctcctgggcc tgggcgtcgc cggcagcgcg ccggggatcg aaggcgacga gatcgcgccg     1800
ctcgccaagg agaacgtggc tgctccttga                                      1830
```

<210> SEQ ID NO 18
<211> LENGTH: 1830
<212> TYPE: DNA
<213> ORGANISM: Artificial Sequence
<220> FEATURE:
<223> OTHER INFORMATION: Nucleic acid sequence of Q427R + E428G mutant
      GBSS1

<400> SEQUENCE: 18

```
atgtcggctc tcaccacgtc ccagctcgcc acctcggcca ccggcttcgg catcgccgac       60
aggtcggcgc cgtcgtcgct gctccgccac gggttccagg gcctcaagcc ccgcagcccc      120
gccggcggcg acgcgacgtc gctcagcctg acgaccagcc gcgcgcgac gcccaagcag      180 cagcggtcgg tgcagcgtgg cagccggagg ttcccctccg tcgtcgtgta cgccaccggc      240
gccggcatga acgtcgtgtt cgtcggcgcc gagatggccc cctggagcaa gaccggcggc      300
ctcggtgacg tcctcggtgg cctcccccct gccatggctg cgaatggcca cagggtcatg      360
```

```
gtgatctctc ctcggtacga ccagtacaag gacgcttggg ataccagcgt tgtggctgag    420
atcaaggttg cagacaggta cgagagggtg aggtttttcc attgctacaa gcgtggagtc    480
gaccgtgtgt tcatcgacca tccgtcattc ctggagaagg tttggggaaa gaccggtgag    540
aagatctacg gacctgacac tggagttgat tacaaagaca accagatgcg tttcagcctt    600
ctttgccagg cagcactcga ggctcctagg atcctaaacc tcaacaacaa cccatacttc    660
aaaggaactt atggtgagga tgttgtgttc gtctgcaacg actggcacac tggcccactg    720
gcgagctacc tgaagaacaa ctaccagccc aatggcatct acaggaatgc aaaggttgct    780
ttctgcatcc acaacatctc ctaccagggc cgtttcgctt cgaggattac cctgagctg     840 aacctctccg agaggttcag gtcatccttc gatttcatcg acgggtatga cacgccggtg    900
gagggcagga agatcaactg gatgaaggcc ggaatcctgg aagccgacag ggtgctcacc    960
gtgagcccgt actacgccga ggagctcatc tccggcatcc caggggatgc gagctcgac    1020 aacatcatgc ggctcaccgg catcaccgga atcgtcaacg gcatggacgt cagcgagtgg   1080
gatcctagca aggacaagta catcaccgcc aagtacgacg caaccacggc aatcgaggcg   1140
aaggcgctga acaaggaggc gttgcaggcg gaggcgggtc ttccggtcga caggaaaatc   1200
ccactgatcg cgttcatcgg caggctggag gaacagaagg gccctgacgt catggccgcc   1260
gccatcccgg agctcatgcg gggggacgtc cagatcgttc ttctgggtac tggaaagaag   1320
aagttcgaga agctgctcaa gagcatggag gagaagtatc cggcaaggt  gagggccgtg   1380 gtgaagttca acgcgccgct tgctcatctc atcatggccg gagccgacgt gctcgccgtc   1440
cccagccgct tcgagccctg tggactcatc cagctgcagg ggatgagata cggaacgccc   1500
tgtgcttgcg cgtccaccgg tgggctcgtg gacacggtca tcgaaggcaa gactggtttc   1560
cacatgggcc gtctcagcgt cgactgcaag gtggtggagc caagcgacgt gaagaaggtg   1620
gcggccaccc tgaagcgcgc catcaaggtc gtcggcacgc cggcgtacga ggagatggtc   1680
aggaactgca tgaaccagga cctctcctgg aaggggcctg cgaagaactg ggagaatgtg   1740
ctcctgggcc tgggcgtcgc cggcagcgcg ccggggatcg aaggcgacga gatcgcgccg   1800
ctcgccaagg agaacgtggc tgctccttga                                    1830

<210> SEQ ID NO 19
<211> LENGTH: 20
<212> TYPE: DNA
<213> ORGANISM: Artificial Sequence
<220> FEATURE:
<223> OTHER INFORMATION: guide-PAM sequence for sgRNA No. 1

<400> SEQUENCE: 19
ggaccatccg tcattcctgg                                                 20

<210> SEQ ID NO 20
<211> LENGTH: 20
<212> TYPE: DNA
<213> ORGANISM: Artificial Sequence
<220> FEATURE:
<223> OTHER INFORMATION: guide-PAM sequence for sgRNA No. 2

<400> SEQUENCE: 20
ggcacactgg cccactggcg                                                 20

<210> SEQ ID NO 21
<211> LENGTH: 20
<212> TYPE: DNA
<213> ORGANISM: Artificial Sequence
```

```
<220> FEATURE:
<223> OTHER INFORMATION: guide-PAM sequence for sgRNA No. 3

<400> SEQUENCE: 21
aagaacaact accagcccaa                                                     20

<210> SEQ ID NO 22
<211> LENGTH: 20
<212> TYPE: DNA
<213> ORGANISM: Artificial Sequence
<220> FEATURE:
<223> OTHER INFORMATION: guide-PAM sequence for sgRNA No. 4

<400> SEQUENCE: 22
tctgcaacga ctggcacact                                                     20

<210> SEQ ID NO 23
<211> LENGTH: 20
<212> TYPE: DNA
<213> ORGANISM: Artificial Sequence
<220> FEATURE:
<223> OTHER INFORMATION: guide-PAM sequence for sgRNA No. A-GBSS10

<400> SEQUENCE: 23
atgcaggagg acgtccagat                                                     20
```

POLYPEPTIDE AND NUCLEIC ACID CAPABLE OF CHANGING AMYLOSE CONTENT (AC) IN PLANT, AND USE THEREOF

CROSS REFERENCE TO THE RELATED APPLICATIONS

This application is a continuation application of International Application No. PCT/CN2021/099676, filed on Jun. 11, 2021, which is based upon and claims priority to Chinese Patent Applications No. 202010543417.8, filed on Jun. 15, 2020, No. 202010657795.9, filed on Jul. 9, 2020, and No. 202110204689.X, filed on Feb. 23, 2021, the entire contents of which are incorporated herein by reference.

TECHNICAL FIELD

The present disclosure belongs to the fields of biotechnology and crop genetic breeding, and specifically relates to a granule-bound starch synthase 1 (GBSS1) mutant protein, and a method and use for reducing or increasing an amylose content (AC) in a plant.

SEQUENCE LISTING

The instant application contains a Sequence Listing which has been submitted in ASCII format via EFS-Web and is hereby incorporated by reference in its entirety. Said ASCII copy is named GBSDSF002-PKG Sequence_Listing.txt, created on Jan. 14, 2022, and is 66,979 bytes in size.

BACKGROUND

*Oryza sativa* is consumed by two-thirds of the world's population and is the main energy source in the diet of at least half of the two-thirds of the world's population. Rice is a low-cost food that is easily and rapidly prepared, which can be eaten together with various dishes.

Rice is mainly composed of carbohydrates and mainly exists in the form of starch (90%) in the endosperm. Starch is widely used in food, papermaking, and chemical industries. Starches can be divided into amylose and amylopectin according to their structures. In rice, granule-bound starch synthase 1 (GBSS1) is encoded by a Waxy (Wx) gene. The gene can control the synthesis of amylose in the endosperm. A natural allelic variation in the Waxy locus is the main reason that affects an amylose content (AC) in rice. AC is a percentage of amylose in a dry weight of polished rice flour, which is one of the key factors that determine the cooking and eating quality of rice. The AC in rice can be extremely low (2% to 9%), low (10% to 20%), medium (20% to 25%), and high (>25%), and the AC in glutinous rice is generally lower than 2%. The AC in the rice endosperm can affect the softness of cooked rice. A too-low AC results in small expansibility and sticky rice; a too-high AC results in large expansibility and hard cooled cooked rice; and a medium AC makes cooked rice relatively soft and results in relatively-high cooking quality. Ratios of amylose to amylopectin in different varieties of rice are very different.

The clustered regularly interspaced short palindromic repeat (CRISPR)/CRISPR-associated (Cas) gene editing technology is a genetic engineering technology emerging in recent years, which is a guide RNA (gRNA)-mediated DNA cleavage technology. A variety of editing systems have been developed for different Cas proteins. A genome editing system can directedly modify a genome, which accelerates the breeding process and is an important technological breakthrough in experimental precision breeding.

The CRISPR/Cas editing technology can achieve four types of targeted editing: 1. Targeted knockout of a gene: A Cas protein recognizes and cleaves a target under the guidance of a gRNA, resulting in a double-stranded DNA break; broken DNA is usually repaired through non-homologous end joining (NHEJ); and during repair, frameshift mutations are easily produced to destroy the gene. 2. Homologous substitution of a target or targeted insertion to change a target sequence: When a double-stranded DNA break is produced, homologous substitution or targeted insertion may occur if there is a homologous repair template nearby. The efficiency of homologous substitution is relatively low, and the longer the length of the sequence to be substituted, the lower the efficiency of homologous substitution. 3. Single-base editing: Single-base editing is a gene editing method where a CRISPR/Cas system is used to make a deaminase target a specific site in a genome to modify a specific base. This method has been successfully used in rice. 4. Genome-guided editing technology: Guided editing is an editing method where a combination of reverse transcriptase and Cas9 nickase is used to achieve a point mutation, an insertion mutation, or a deletion mutation under the guidance of a single-stranded gRNA according to a transcription template.

Therefore, there is an urgent need in the art to mutate the waxy gene by a gene editing technology to change the AC, for example, to reduce or increase the AC, thereby improving the eating quality of rice.

SUMMARY

The present disclosure is intended to provide a mutant GBSS1 polypeptide capable of reducing or increasing an AC in a plant, a polynucleotide encoding the protein or a fragment thereof, and use thereof.

In an aspect, the present disclosure provides a mutant GBSS1 polypeptide, and compared to an amino acid sequence of a parent GBSS1, the mutant GBSS1 polypeptide has mutation at amino acid corresponding to amino acid 168 of an amino acid sequence shown in SEQ ID NO: 1. In an embodiment, the amino acid 168 may be proline (P).

In another aspect, the present disclosure provides a mutant GBSS1 polypeptide, and compared to an amino acid sequence of a parent GBSS1, the mutant GBSS1 polypeptide has mutation at amino acid corresponding to amino acid 237 of the amino acid sequence shown in SEQ ID NO: 1. In an embodiment, the amino acid 237 may be threonine (T).

In another aspect, the present disclosure provides a mutant GBSS1 polypeptide, and compared to an amino acid sequence of a parent GBSS1, the mutant GBSS1 polypeptide has mutations at amino acids corresponding to amino acid 168 and amino acid 237 of the amino acid sequence shown in SEQ ID NO: 1. In an embodiment, the amino acid 168 may be proline (P); and the amino acid 237 may be threonine (T).

In an embodiment, the proline (P) at position 168 may be mutated into an amino acid other than proline (P), and the amino acid other than proline (P) may be one or more selected from the group consisting of alanine (A), valine (V), glycine (G), leucine (L), isoleucine (I), phenylalanine (F), tryptophan (W), tyrosine (Y), aspartic acid (D), asparagine (N), lysine (K), glutamine (Q), methionine (M), serine (S), threonine (T), cysteine (C), histidine (H), glutamic acid (E), and arginine (R).

In a preferred embodiment, the proline (P) at position 168 may be mutated into leucine (L).

In an embodiment, the threonine (T) at position 237 may be mutated into an amino acid other than threonine (T), and the amino acid other than threonine (T) may be one or more selected from the group consisting of alanine (A), valine (V), glycine (G), leucine (L), isoleucine (I), phenylalanine (F), tryptophan (W), tyrosine (Y), aspartic acid (D), asparagine (N), lysine (K), glutamine (Q), methionine (M), serine (S), proline (P), cysteine (C), histidine (H), glutamic acid (E), and arginine (R).

In a preferred embodiment, the threonine (T) at position 237 may be mutated into alanine (A).

In another aspect, the present disclosure provides a mutant GBSS1 polypeptide, and compared to an amino acid sequence of a parent GBSS1, the mutant GBSS1 polypeptide has mutation at amino acid corresponding to one or more of amino acid 411, amino acid 410, and amino acid 236 of the amino acid sequence shown in SEQ ID NO: 1.

The amino acid 411 may be E, and preferably, the amino acid 411 may be mutated into K.

The amino acid 410 may be E, and preferably, the amino acid 410 may be mutated into K.

The amino acid 236 may be H, and preferably, the amino acid 236 may be mutated into R.

In another aspect, the present disclosure provides a mutant nucleic acid of GBSS1, and the mutant nucleic acid has a sequence shown in any one from the group consisting of SEQ ID NOS: 9-12 (three bases encoding L at position 409 are mutated into cta, three bases encoding Q at position 412 are mutated into caa, three bases encoding E at position 410 are mutated into gaa, and three bases encoding E at position 411 are mutated into aaa). In an embodiment, the above-mentioned mutant GBSS1 polypeptide may further include other mutation sites, which may be one or more selected from the group consisting of positions 159, 178, 236, 265, 268, 353, 408, 410, 413, and 487 corresponding to the amino acid sequence shown in SEQ ID NO: 1; and the other mutation sites can maintain or reduce the AC in a plant.

In another aspect, the present disclosure provides a mutant GBSS1 polypeptide, and compared to an amino acid sequence of a parent GBSS1, the mutant GBSS1 polypeptide has mutation at amino acids corresponding to amino acid 427 and/or amino acid 428 of the amino acid sequence shown in SEQ ID NO: 1.

In an embodiment, in the parent GBSS1, the amino acid 427 may be glutamine (Q) and the amino acid 428 may be glutamic acid (E).

In an embodiment, the glutamine (Q) at position 427 may be mutated into an amino acid other than glutamine (Q), and the amino acid other than glutamine (Q) may be one or more selected from the group consisting of alanine (A), valine (V), glycine (G), leucine (L), isoleucine (I), phenylalanine (F), tryptophan (W), tyrosine (Y), aspartic acid (D), asparagine (N), glutamic acid (E), lysine (K), methionine (M), serine (S), threonine (T), cysteine (C), proline (P), histidine (H), and arginine (R).

In a preferred embodiment, the glutamine (Q) at position 427 may be mutated into arginine (R).

In an embodiment, the glutamic acid (E) at position 428 may be mutated into an amino acid other than glutamic acid (E), and the amino acid other than glutamic acid (E) may be one or more selected from the group consisting of alanine (A), valine (V), glycine (G), leucine (L), isoleucine (I), phenylalanine (F), tryptophan (W), tyrosine (Y), aspartic acid (D), asparagine (N), lysine (K), glutamine (Q), methionine (M), serine (S), threonine (T), cysteine (C), proline (P), histidine (H), and arginine (R).

In a preferred embodiment, the glutamic acid (E) at position 428 may be mutated into glycine (G).

In an embodiment, the mutation may be selected from the group consisting of Q427R, E428G, and a combination thereof.

In an embodiment, the parent GBSS1 may be derived from any plant; and preferably, may be derived from a monocotyledonous plant or a dicotyledonous plant.

In an embodiment, the parent GBSS1 polypeptide may be derived from one or more selected from the group consisting of a gramineous plant, a leguminous plant, a chenopodiaceous plant, and a cruciferous plant.

In an embodiment, the parent GBSS1 polypeptide may be derived from one or more selected from the group consisting of *Arabidopsis thaliana* (*A. thaliana*), *Oryza sativa*, *Nicotiana tabacum*, *Zea mays*, *Sorghum bicolor*, *Hordeum vulgare*, *Triticum aestivum*, *Setaria italica*, *Glycine max*, *Lycopersicon esculentum*, *Solanum tuberosum*, *Chenopodium quinoa*, *Lactuca sativa*, *Brassica napus*, *Brassica pekinensis*, and *Fragaria ananassa*.

In a preferred embodiment, the wild-type GBSS1 of the present disclosure may be derived from *Oryza* L., especially *Oryza sativa*.

In an embodiment, the parent GBSS1 protein may have GBSS1 activity, and an amino acid sequence of the parent GBSS1 may have at least 80%, at least 85%, at least 90%, at least 95%, at least 96%, at least 97%, at least 98%, or at least 99% sequence identity with the amino acid sequence shown in SEQ ID NO: 1.

In a preferred embodiment, the amino acid sequence of the parent GBSS1 may have the sequence shown in SEQ ID NO: 1, or the amino acid sequence of the parent GBSS1 may be shown in SEQ ID NO: 1.

In an embodiment, the mutant polypeptide may have at least 60%, preferably at least 70%, preferably at least 80%, and preferably at least 90% (such as 95%, 97%, or 99%) homology with a sequence shown in any one of SEQ ID NOS: 2-4 or 13-15.

In an embodiment, the mutant polypeptide may be a polypeptide with an amino acid sequence shown in any one of SEQ ID NOS: 2-4 or 13-15, an active fragment thereof, or a conservative variant polypeptide thereof.

In an embodiment, the mutant polypeptide may have an amino acid sequence shown in any one of SEQ ID NOS: 2-4 or 13-15.

In another aspect, the present disclosure provides a polynucleotide encoding the mutant GBSS1 protein or an active fragment thereof.

In an embodiment, the polynucleotide may be selected from the group consisting of:
   (a) a polynucleotide encoding the polypeptide shown in any one of SEQ ID NOS: 2-4 or 13-15;
   (b) a polynucleotide with a sequence shown in any one of SEQ ID NOS: 5-7 or 16-18;
   (c) a polynucleotide that has a nucleotide sequence of homology ≥80% (preferably ≥90%, more preferably ≥95%, and most preferably ≥98%) with a sequence shown in SEQ ID NO: 5 and encodes a polypeptide shown in SEQ ID NO: 2; or, a polynucleotide that has a nucleotide sequence of homology ≥80% (preferably ≥90%, more preferably ≥95%, and most preferably ≥98%) with a sequence shown in SEQ ID NO: 6 and encodes a polypeptide shown in SEQ ID NO: 3; or, a polynucleotide that has a nucleotide sequence of homology ≥80% (preferably ≥90%, more preferably ≥95%, and most preferably ≥98%) with a sequence shown in SEQ ID NO: 7 and encodes a polypeptide shown in SEQ ID NO: 4; or, a polynucleotide that has a nucleotide sequence of homology ≥80% (preferably ≥90%, more preferably ≥95%, and most preferably ≥98%) with a sequence shown in SEQ ID NO: 16 and encodes a polypeptide shown in SEQ ID NO: 13; or, a polynucleotide that has a nucleotide sequence of homology ≥80% (preferably ≥90%, more preferably ≥95%, and most preferably ≥98%) with a sequence shown in SEQ ID NO: 17 and encodes a polypeptide shown in SEQ ID NO: 14; or, a polynucleotide that has a nucleotide sequence of homology ≥80% (preferably ≥90%, more preferably ≥95%, and most preferably ≥98%) with a sequence shown in SEQ ID NO: 18 and encodes a polypeptide shown in SEQ ID NO: 15; and (d) a polynucleotide complementary to any one selected from the group consisting of the polynucleotides described in (a) to (c).

In an embodiment, the polynucleotide may be selected from the group consisting of a genomic sequence, a cDNA sequence, an RNA sequence, and a combination thereof.

In an embodiment, the polynucleotide may preferably be single-stranded or double-stranded.

In an embodiment, the polynucleotide may make an auxiliary element selected from the group consisting of a signal peptide, a secretory peptide, a tag sequence (such as 6His), and a combination thereof additionally included at a flank of an open reading frame (ORF) of the mutant polypeptide.

In an embodiment, the polynucleotide may further include a promoter operably linked to the ORF sequence of the mutant polypeptide.

In an embodiment, the promoter may be selected from the group consisting of a constitutive promoter, a tissue-specific promoter, an inducible promoter, and a strong promoter.

In another aspect, the present disclosure provides a fusion protein including the mutant GBSS1 protein of the present disclosure. The fusion protein includes, but not limited to, a tag peptide, a histidine tag, 6×His, or a plastid-targeted peptide, a chloroplast-targeted peptide, or a regulatory element, a promoter sequence, a terminator sequence, a leader sequence, a polyadenylation sequence, and a marker gene.

In another aspect, the present disclosure also provides a vector including a nucleic acid sequence encoding the mutant GBSS1 or the fusion protein of the present disclosure or the mutant nucleic acid (any one of SEQ ID NOS: 9-12). Preferably, the vector may further include an expression regulation element operably linked to the aforementioned nucleic acid sequence.

In an embodiment, the vector may include an expression vector, a shuttle vector, and an integration vector.

In an embodiment, the vector may also be a vector for gene editing of the endogenous GBSS1 gene in a host cell.

In an embodiment, the vector may include a polynucleotide encoding a polypeptide shown in any one of SEQ ID NOS: 2-4 or 13-15.

In an embodiment, the expression vector may also include at least one replication origin to realize self-replication.

In an embodiment, the vector may be a vector that will be integrated into a genome of a host cell when introduced into the host cell and then replicates together with a chromosome into which the vector is integrated.

The vector can be, for example, a plasmid, a virus, a cosmid, a phage, and the like, which are well known to those skilled in the art.

Preferably, the expression vector in the present disclosure may be a plasmid.

In another aspect, the present disclosure provides a nucleic acid construct, including the polynucleotide and a regulatory element operably linked thereto.

In an embodiment, the regulatory element may be one or more selected from the group consisting of an enhancer, a transposon, a promoter, a terminator, a leader sequence, a polyadenylate sequence, and a marker gene.

In another aspect, the present disclosure provides a host cell, where the host cell includes the nucleic acid construct or the vector, or a genome of the host cell is integrated with the polynucleotide.

In an embodiment, the host cell may be a eukaryotic cell, such as a yeast cell, an animal cell, or a plant cell.

In an embodiment, the host cell may be a prokaryotic cell, such as *Escherichia coli* (*E. coli*).

In an embodiment, the plant may include an angiosperm and a gymnosperm.

In an embodiment, the plant may include a monocotyledonous plant and a dicotyledonous plant.

In an embodiment, the plant may include an herbaceous plant and a woody plant.

In an embodiment, the plant may include *A. thaliana, Nicotiana tabacum, Oryza sativa, Zea mays, Sorghum bicolor, Hordeum vulgare, Triticum aestivum, Setaria italica, Glycine max, Lycopersicon esculentum, Solanum tuberosum, Chenopodium quinoa, Lactuca sativa, Brassica napus, Brassica pekinensis*, and *Fragaria ananassa*.

In another aspect, the present disclosure provides a method for preparing the mutant GBSS1 polypeptide or an active fragment thereof, including the following step:

(a) under conditions suitable for expression, cultivating a host cell including the mutant GBSS1 polypeptide to express the mutant GBSS1 polypeptide; and preferably, the method may further include:

(b) isolating the mutant GBSS1 polypeptide.

In another aspect, the present disclosure provides a method for changing an AC in a plant or a method for preparing a plant with a changed AC, including the following: introducing the mutant polypeptide described above into a plant cell, a plant seed, a plant tissue, a plant part, or a plant.

In another aspect, the present disclosure also provides use of the mutant polypeptide, the polynucleotide, the nucleic acid construct, or the host cell described above in the preparation of a plant with a changed AC.

In another aspect, the present disclosure provides a plant cell, a plant seed, a plant tissue, a plant part, or a plant with low AC, where the plant cell, the plant tissue, the plant seed, the plant part, or the plant includes the mutant GBSS1 polypeptide or a polynucleotide sequence encoding the same, or includes the mutant nucleic acid (shown in any one of SEQ ID NOS: 9-12); and compared to an amino acid sequence of a parent GBSS1, the mutant GBSS1 polypeptide has mutation at amino acid corresponding to one or more of amino acid 237, amino acid 168, and amino acid 411 of the amino acid sequence shown in SEQ ID NO: 1.

In another aspect, the present disclosure provides a method for reducing an AC in a plant, including the following step: introducing the GBSS1 mutant polypeptide into a plant cell, a plant seed, a plant tissue, a plant part, or a plant; preferably, the reducing an AC in a plant may refer to reducing an AC in a plant seed; and compared to an amino acid sequence of a parent GBSS1, the mutant GBSS1 polypeptide has mutation at amino acid corresponding to one or more of amino acid 237, amino acid 168, and amino acid 411 of the amino acid sequence shown in SEQ ID NO: 1.

In another aspect, the present disclosure also provides a method for preparing a plant with low AC, including: introducing the GBSS1 mutant polypeptide or the mutant nucleic acid (shown in any one of SEQ ID NOS: 9-12) into a plant cell, a plant seed, a plant tissue, a plant part, or a plant; and compared to an amino acid sequence of a parent GBSS1, the mutant GBSS1 polypeptide has mutation at amino acid corresponding to one or more of amino acid 237, amino acid 168, and amino acid 411 of the amino acid sequence shown in SEQ ID NO: 1.

In another aspect, the present disclosure provides a plant cell, a plant seed, a plant tissue, a plant part, or a plant with high AC, where the plant cell, the plant tissue, the plant seed, the plant part, or the plant includes the mutant GBSS1 polypeptide or a polynucleotide sequence thereof; and compared to an amino acid sequence of a parent GBSS1, the mutant GBSS1 polypeptide has mutation at amino acid corresponding to amino acid 427 and/or amino acid 428 of the amino acid sequence shown in SEQ ID NO: 1.

The low AC or the reducing AC means that a plant carrying the mutant GBSS1 can have reduced AC compared with a plant carrying the parent GBSS1.

In another aspect, the present disclosure also provides use of the above-mentioned plant cell, plant seed, plant tissue, plant part, or plant with high AC in the production of amylose.

In another aspect, the present disclosure provides a method for increasing an AC in a plant, including the following step: introducing the GBSS1 mutant polypeptide into a plant cell, a plant seed, a plant tissue, a plant part, or a plant; preferably, the increasing an AC in a plant may refer to increasing an AC in a plant seed; and compared to an amino acid sequence of a parent GBSS1, the mutant GBSS1 polypeptide has mutation at amino acid corresponding to amino acid 427 and/or amino acid 428 of the amino acid sequence shown in SEQ ID NO: 1.

In another aspect, the present disclosure also provides a method for preparing a plant with high AC, including the following: introducing the GBSS1 mutant polypeptide into a plant cell, a plant seed, a plant tissue, a plant part, or a plant; and compared to an amino acid sequence of a parent GBSS1, the mutant GBSS1 polypeptide has mutation at amino acid corresponding to amino acid 427 and/or amino acid 428 of the amino acid sequence shown in SEQ ID NO: 1.

The high AC or the increasing AC means that a plant carrying the mutant GBSS1 can have increased AC compared with a plant carrying the parent GBSS1.

In an embodiment, the introducing the GBSS1 mutant polypeptide of the present disclosure may include the following step: allowing the GBSS1 mutant polypeptide to express in the plant cell, the plant seed, the plant tissue, the plant part, or the plant. For example, the mutant polypeptide is expressed by an expression vector, or the mutant polypeptide is integrated into a plant genome for expression.

In a preferred embodiment, the above method may include the following steps:
(1) providing *Agrobacterium tumefaciens* (*A. tumefaciens*) carrying an expression vector, where the expression vector includes a DNA coding sequence of the mutant GBSS1 polypeptide or an active fragment thereof;
(2) contacting the plant cell, the plant tissue, or the plant part with the *A. tumefaciens* in step (1), such that the DNA coding sequence of the mutant GBSS1 polypeptide or the active fragment thereof is transformed into the plant cell and integrated on a chromosome of the plant cell; and
(3) screening out a plant cell transformed with the DNA coding sequence of the mutant GBSS1 polypeptide or the active fragment thereof.

In an embodiment, the introducing the mutant GBSS1 polypeptide may include the following step: allowing endogenous GBSS1 of the plant to mutate to introduce the mutant polypeptide.

Preferably, an amino acid sequence of the endogenous GBSS1 may have at least 80%, at least 85%, at least 90%, at least 95%, at least 96%, at least 97%, at least 98%, or at least 99% sequence identity with the amino acid sequence shown in SEQ ID NO: 1.

In a preferred embodiment, the amino acid sequence of the endogenous GBSS1 may have the sequence shown in SEQ ID NO: 1, or the amino acid sequence of the endogenous GBSS1 may be shown in SEQ ID NO: 1.

In another preferred embodiment, the method may include the following: allowing an endogenous GBSS1 coding sequence in the plant cell, the plant seed, the plant tissue, or the plant part to mutate at positions corresponding to one or more amino acids selected from the group consisting of amino acid 237, amino acid 168, amino acid 411, amino acid 410, and amino acid 236 of SEQ ID NO: 1, or corresponding to amino acid 427 and/or amino acid 428 of SEQ ID NO: 1.

In another preferred embodiment, the method may include the following steps:
(1) introducing an expression vector carrying a gene editing tool into the plant cell, the plant seed, the plant tissue, or the plant part; and
(2) allowing the gene editing tool to act on an endogenous GBSS1 coding sequence, such that the endogenous GBSS1 coding sequence mutates at amino acid corresponding to one or more of amino acids 237, 168, 411, 410, and 236 of SEQ ID NO: 1, or, the endogenous GBSS1 coding sequence mutates at amino acid corresponding to amino acid 427 and/or amino acid 428 of SEQ ID NO: 1.

Further, the above method may also include the following step: screening a mutant plant cell, plant tissue, or plant part, and optionally, isolating the gene editing tool.

In a preferred embodiment, the gene editing tool may include CRISPR, transcription activator-like effector nuclease (TALEN), and zinc-finger nuclease (ZFN).

In another aspect, the present disclosure also provides use of the mutant polypeptide, the polynucleotide, the fusion protein, the vector, the nucleic acid construct, or the host cell in the preparation of a plant with low AC; and compared to an amino acid sequence of a parent GBSS1, the mutant GBSS1 polypeptide has mutation at amino acid corresponding to one or more of amino acid 237, amino acid 168, and amino acid 411 of the amino acid sequence shown in SEQ ID NO: 1.

In another aspect, the present disclosure also provides use of the mutant polypeptide, polynucleotide, fusion protein, vector, nucleic acid construct, or host cell in the preparation of a plant with high AC; and compared to an amino acid sequence of a parent GBSS1, the mutant GBSS1 polypeptide has mutation at amino acid corresponding to amino acid 427 and/or amino acid 428 of the amino acid sequence shown in SEQ ID NO: 1.

In another aspect, the present disclosure also provides use of a plant prepared by the above preparation method in the production of amylose.

In another aspect, the present disclosure also provides a method for preparing amylose from a plant, where the plant is prepared by the preparation method described above.

In a preferred embodiment, the plant may include an angiosperm and a gymnosperm.

In another preferred embodiment, the plant may include a monocotyledonous plant and a dicotyledonous plant.

In another preferred embodiment, the plant may include an herbaceous plant and a woody plant.

In another preferred embodiment, the plant may include *A. thaliana*, *Nicotiana tabacum*, *Oryza sativa*, *Zea mays*, *Sorghum bicolor*, *Hordeum vulgare*, *Triticum aestivum*, *Setaria italica*, *Glycine max*, *Lycopersicon esculentum*, *Solanum tuberosum*, *Chenopodium quinoa*, *Lactuca sativa*, *Brassica napus*, *Brassica pekinensis*, and *Fragaria ananassa*.

In another aspect, the present disclosure provides use of the mutant polypeptide, polynucleotide, fusion protein, vector, nucleic acid construct, or host cell in a reagent or a kit for preparing a plant with low AC.

General Definitions

Unless defined otherwise, the technical and scientific terms used herein have the same meanings as commonly understood by one of ordinary skill in the art.

The terms "polynucleotide", "nucleotide sequence", "nucleic acid sequence", "nucleic acid molecule", and "nucleic acid" may be used interchangeably and include DNA, RNA, or a hybrid thereof, which may be double-stranded or single-stranded.

The term "homology" or "identity" used refers to sequence matching between two polypeptides or between two nucleic acids. Therefore, the composition and method of the present disclosure also include homologues of the nucleotide sequence and the polypeptide sequence (such as SEQ ID NOS: 1-7) of the present disclosure. "Homology" can be calculated by a known method including but not limited to: Computational Molecular Biology (edited by Lesk, A. M.), Oxford University Press, New York (1988); Biocomputing: Informatics and Genome Projects (edited by Smith, D. W.), Academic Press, New York (1993); Computer Analysis of Sequence Data, Part I (edited by Griffin, A. M. and Griffin, H. G.), Humana Press, New Jersey (1994); Sequence Analysis in Molecular Biology (edited by von Heinje, G.), Academic Press (1987); and Sequence Analysis Primer (edited by Gribskov, M. and Devereux, J.), Stockton Press, New York (1991).

The term "encoding" refers to an inherent characteristic of a specific nucleotide sequence in a polynucleotide, such as a gene cDNA or mRNA, which serves as a template for the synthesis of a defined nucleotide sequence (namely, rRNA, tRNA, and mRNA) or a defined amino acid sequence and the synthesis of other polymers and macromolecules in a biological process of a biological characteristic thereof. Therefore, if the transcription and translation of mRNA corresponding to a gene produces a protein in a cell or another biological system, the gene encodes the protein.

The term "amino acid" refers to a carboxylic acid with amino. Various proteins in organisms are composed of 20 essential amino acids.

The terms "protein", "polypeptide", and "peptide" can be used interchangeably in the present disclosure and refer to a polymer of amino acid residues, including a polymer in which one or more amino acid residues are a chemical analogue of a natural amino acid residue. The protein and polypeptide of the present disclosure can be produced through recombination or chemical synthesis. The term "mutant protein" refers to a protein that is obtained through substitution, insertion, deletion, and/or addition of one or more amino acid residues based on an amino acid sequence of a parent protein.

The term "AxxB" means that amino acid A at position xx is changed into amino acid B. For example, P168L means that proline (P) at position 168 is changed into leucine (L), T237A means that threonine (T) at position 237 is changed into alanine (A), Q427R means that glutamine (Q) at position 427 is changed into arginine (R), E428G means that glutamic acid (E) at position 428 is changed into glycine (G), and so on. For double or multiple mutations, mutations are separated by a "/". For example, Q427R/E428G indicates that, relative to the amino acid sequence of SEQ ID NO: 1, glutamine (Q) at position 427 is substituted by arginine (R) and glutamic acid (E) at position 428 is substituted by glycine (G), where both mutations are present in the specific mutant GBSS1 protein.

The term "regulatory element" in the present disclosure refers to a nucleic acid sequence capable of regulating the transcription and/or translation of a nucleic acid operably linked thereto. The regulatory element includes a promoter sequence, a terminator sequence, a leader sequence, a polyadenylation sequence, a signal peptide coding region, a marker gene, and the like.

The term "vector" refers to an element that is allowed to be integrated into a genome of a host cell or to self-replicate within a cell independently of its genome. The vector may include any elements that guarantee the self-replication. The vector usually carries a gene that is not a part of the central metabolism of a cell and is usually in the form of double-stranded DNA. The selection of a vector generally depends on the compatibility of the vector with a host cell into which the vector is to be introduced. When a vector needs to be used, the selection of the vector depends on a method for transforming a host cell well known to those skilled in the art. For example, a plasmid vector can be used.

The term "GBSS1" refers to granule-bound starch synthase 1 encoded by the *Oryza sativa* waxy gene (waxy).

The term "parent GBSS1 polypeptide" refers to a polypeptide derived from the GBSS1 mutant polypeptide. In a preferred embodiment, the parent GBSS1 polypeptide is a protein (polypeptide) that can be found in nature or is encoded by a nucleic acid that can be found in nature, where nucleotides of the nucleic acid can be obtained through genetic engineering such as genome sequencing and polymerase chain reaction (PCR), and an amino acid sequence of the protein can be deduced from the nucleotide sequence. An amino acid sequence of the wild-type GBSS1 polypeptide is shown in SEQ ID NO: 1, for example. In some embodiments, the parent GBSS1 polypeptide may be obtained by changing one or more amino acid residues of the wild-type GBSS1 polypeptide without affecting the enzymatic activity.

The terms "mutant GBSS1 polypeptide", "mutant GBSS1 protein", "mutant GBSS1 enzyme", "mutant protein", "mutant polypeptide", "polypeptide of the present disclosure", and the like can be used interchangeably. Preferably, the mutant GBSS1 polypeptide has mutation at amino acid corresponding to amino acid 168 and/or amino acid 237 of the sequence shown in SEQ ID NO: 1, or, the mutant GBSS1 polypeptide has mutation at amino acid corresponding to amino acid 427 and/or amino acid 428 of the sequence shown in SEQ ID NO: 1.

The term "amylose" refers to a linear polymer composed of glucose, where glucose monomers are mainly linked through α(1→4) glycosidic bonds, and each amylose molecule usually includes thousands of glucose monomers. Amylose and amylopectin are common starches in organisms. The α(1→4) glycosidic bond leads to a helical structure of amylose. Amylose usually has 300 to 3,000 of repeating glucose monomers.

The hydrolysis and digestion of amylose is slower than that of amylopectin. However, as an energy storage substance, amylose occupies less space, and thus about 20% of starch in plants is amylose. Amylase is at an end of an amylose molecule and breaks up amylose into glucose monomers through hydrolysis. Because amylopectin has many ends, a relative hydrolysis speed is relatively high.

The low AC means that the AC in the plant (especially the plant seed) is at least 50% (preferably 60%, 70%, 80%, or 90%) lower than that in the parent plant.

The high AC means that the AC in the plant (especially the plant seed) is at least 50% (preferably 60%, 70%, 80%, 90%, 100%, 110%, 120%, 130%, 140%, or 150%) than that in the parent plant.

The term "AC" is a percentage of amylose in a dry weight of a polished rice flour, which is one of the key factors that determine the cooking and eating quality of rice. The AC in rice can be extremely low (2% to 9%), low (10% to 20%), medium (20% to 25%), and high (>25%), and the AC in glutinous rice is generally lower than 2%. The AC in the rice endosperm can affect the softness of cooked rice. A too-low AC results in small expansibility and sticky rice; a too-high AC results in large expansibility and hard cooled cooked rice; and a medium AC makes cooked rice relatively soft and results in relatively-high cooking quality.

The term "host organism" should be understood as any unicellular or multicellular organism into which a nucleic acid encoding the mutant GBSS1 protein can be introduced, including, for example, bacteria such as *E. coli*, fungi such as yeast (such as *Saccharomyces cerevisiae* (*S. cerevisiae*)), molds (such as *Aspergillus*), plant cells, and plants.

The term "plant" should be understood as any differentiated multicellular organism capable of photosynthesis, including: crop plants at a mature or developmental stage, especially monocotyledonous or dicotyledonous plants; vegetable crops including artichoke, turnip cabbage, arugula, leek, asparagus, lettuce (such as head lettuce, leaf lettuce, and romaine lettuce), bok choy, malanga, melons (such as cantaloupe, watermelon, crenshaw melon, honeydew melon, and Roman cantaloupe), rape crops (such as Brussels sprout, cabbage, cauliflower, broccoli, borecole, kale, Chinese cabbage, and bok choy), cardoon, carrot, napa, okra, onion, celery, parsley, chickpea, parsnip, chicory, pepper, *Solanum tuberosum*, gourd (such as marrow squash, cucumber, zucchini, cushaw, and pumpkin), radish, dried ball onion, rutabaga, purple eggplant (also known as eggplant), salsify, lettuce, shallot, endive, garlic, spinach, green onion, cushaw, greens, beets (sugar beets and fodder beets), sweet potato, Swiss chard, wasabi, tomato, turnip, and spices; fruits and/or vine crops such as apple, apricot, cherry, nectarine, peach, pear, plum, prune, cherry, quince, almond, chestnut, hazelnut, pecan, pistachio, walnut, citrus, blueberry, boysenberry, cranberry, currant, loganberry, raspberry, strawberry, blackberry, grape, avocado, banana, kiwi, persimmon, pomegranate, pineapple, tropical fruit, pome, melon, mango, *papaya*, and lychee; field crops, such as clover, alfalfa, evening primrose, meadowfoam, corn/maize (forage corn, sweet corn, and popcorn), *lupulus*, jojoba, peanut, rice, safflower, small grain crops (*Hordeum vulgare*, oat, rye, *Triticum aestivum*, and the like), *Sorghum bicolor*, *Nicotiana tabacum*, kapok, legumes (beans, lentil, pea, and *Glycine max*), oil plants (canola, leaf mustard, poppy, olive, sunflower, coconut, castor oil plant, cocoa bean, and groundnut), *Arabidopsis*, fiber plants (cotton, flax, hemp, and jute), Lauraceae (cinnamon or camphor), or a plant such as coffee, sugar cane, tea, and natural rubber plants; and/or bedding plants such as a flowering plant, cactus, a succulent plant, and/or an ornamental plant, and trees such as forests (broad-leaved and evergreen trees, such as conifers), fruit trees, ornamental trees, nut-bearing trees, shrubs, and other seedlings.

The term "plant tissue" or "plant part" includes a plant cell, a protoplast, a plant tissue culture, a plant callus, a plant piece, a plant embryo, a pollen, an ovule, a seed, a leaf, a stem, a flower, a branch, a seedling, a fruit, a nucleus, a spike, a root, a root tip, an anther, and the like.

The term "plant cell" should be understood as any cell derived or found in a plant, which is capable of forming, for example, undifferentiated tissues such as calli, differentiated tissue such as embryos, constituent parts of a plants, plants, or seeds.

The gene editing technology includes CRISPR technology, TALEN technology, and ZFN technology. "CRISPR" refers to clustered regularly interspaced short palindromic repeat, which comes from the immune system of microorganisms. A gene editing tool includes gRNA and Cas protein (such as Cas9, Cpf1, and Cas12b). The gene editing tool of TALEN refers to a restriction enzyme that can cleave a specific DNA sequence, which includes a TAL effector DNA binding domain and a DNA cleavage domain. The gene editing tool of ZFN refers to a restriction enzyme that can cleave a specific DNA sequence, which includes a zinc-finger DNA binding domain and a DNA cleavage domain. It is well known to those skilled in the art that an intracellular genome can be edited by constructing nucleotides encoding a gene editing tool and other regulatory elements into a suitable vector and then transforming the vector into a cell; and a type of the editing includes gene knockout, insertion, and base editing.

In the present disclosure, the wild-type GBSS1 can be derived from any plant, especially the aforementioned monocotyledonous or dicotyledonous plants. Wild-type GBSS1 sequences and coding sequences thereof from some sources have been disclosed in some existing technical literatures, and these technical literatures are hereby incorporated herein by reference.

Preferably, the wild-type GBSS1 of the present disclosure may be derived from *Oryza* L., especially *Oryza sativa*. More preferably, the wild-type GBSS1 may have an amino acid sequence shown in SEQ ID NO: 1, or may have an amino acid sequence of at least 80%, at least 85%, at least 90%, at least 95%, at least 96%, at least 97%, at least 98%, or at least 99% sequence identity with the amino acid sequence shown in SEQ ID NO: 1.

For example, it is clear to those skilled in the art that a structure of a protein can be changed without adversely affecting the activity and functionality of the protein. For example, one or more conservative amino acid substitutions can be introduced into an amino acid sequence of a protein without adversely affecting the activity and/or three-dimensional (3D) configuration of the protein molecule. Those skilled in the art are aware of examples and implementations of the conservative amino acid substitutions. Specifically, an amino acid residue can be substituted by another amino acid residue that belongs to the same group as the amino acid residue to be substituted. That is, a nonpolar amino acid residue can be substituted by another nonpolar amino acid residue; an uncharged polar amino acid residue can be substituted by another uncharged polar amino acid residue; a basic amino acid residue can be substituted by another basic amino acid residue; and an acidic amino acid residue can be substituted by another acidic amino acid residue. Such substituted amino acid residues may be or may not be encoded by genetic codes. As long as a substitution does not damage the biological activity of a protein, a conservative substitution in which an amino acid is substituted by another amino acid belonging to the same group falls within the scope of the present disclosure. Therefore, in addition to the above-mentioned mutations, the mutant GBSS1 protein of the present disclosure may include one or more other mutations such as conservative substitutions in the amino acid sequence. In addition, the present disclosure covers mutant GBSS1 proteins with one or more other non-conservative substitutions, as long as the non-conservative substitutions do not significantly affect the desired function and biological activity of the protein of the present disclosure.

As well known in the art, one or more amino acid residues can be deleted from the N and/or C terminus of a protein while still retaining its functional activity. Therefore, in another aspect, the present disclosure also relates to a fragment that is obtained through deletion of one or more amino acid residues from the N-terminus and/or C-terminus of the mutant GBSS1 protein and retains the required functional activity (such as an amino acid fragment with the mutation site of the present disclosure), which is also within the scope of the present disclosure and is called a biologically-active fragment. In the present disclosure, the "biologically-active fragment" refers to a part of the mutant GBSS1 protein of the present disclosure, which retains the biological activity of the mutant GBSS1 protein of the present disclosure. For example, the biologically-active fragment of the mutant GBSS1 protein may be obtained after one or more (for example, 1-50, 1-25, 1-10, or 1-5, such as 1, 2, 3, 4, or 5) amino acid residues are deleted from the N-terminus and/or C-terminus of the protein, which still retains the biological activity of the full-length protein.

In addition, the mutant protein of the present disclosure can also be modified. Modified (usually without changing the primary structure) forms may include the following: chemically derived forms of the mutant protein in vivo or in vitro, such as acetylated or carboxylated form. The modification may also include glycosylation, such as glycosylation modification during the synthesis and processing or further processing of the mutant protein to produce a mutant protein. The modification can be accomplished by exposing the mutant protein to a glycosylase (such as a mammalian glycosylase or deglycosylase). The modified forms may also include sequences with phosphorylated amino acid residues (such as phosphotyrosine, phosphoserine, and phosphothreonine). The mutant protein can also be modified to reduce its proteolysis resistance or optimize its solubility.

The present disclosure also provides a polynucleotide encoding the mutant GBSS1 polypeptide, which may also include additional coding and/or non-coding sequences. Preferably, the mutant GBSS1 polypeptide may be shown in any one of SEQ ID NOS: 2-4 or 13-15. Those skilled in the art are well aware that, due to the degeneracy of genetic codes, there are many different nucleic acid sequences that can encode the amino acid sequence disclosed herein. Producing other nucleic acid sequences encoding the same protein is within the competence scope of those of ordinary skill in the art, and thus the present disclosure covers nucleic acid sequences encoding the same amino acid sequence due to the degeneracy of genetic codes. For example, in order to achieve the high expression of a heterologous gene in a target host organism such as a plant, the gene can be optimized using a codon preferred by the host organism to allow better expression.

The full-length sequence of the polynucleotide of the present disclosure can usually be obtained through PCR amplification, recombination, or artificial synthesis. For the PCR amplification, primers can be designed according to the relevant nucleotide sequence disclosed in the present disclosure, especially the ORF sequence, and a commercially available cDNA library or a cDNA library prepared by a conventional method known to those skilled in the art can be used as a template to amplify the relevant sequence. When the sequence is long, it is often necessary to conduct two or more PCR amplifications, and then amplified fragments are spliced together in a correct order. The obtained nucleotide sequence can be cloned into a vector and then transformed into a cell, and then a large number of related sequences can be isolated from proliferated host cells by a conventional method. The mutation site of the present disclosure can also be introduced through artificial synthesis.

One or more copies of the polynucleotide of the present disclosure can be inserted into a host cell to increase a yield of a gene product. The copy number of the polynucleotide can be increased by integrating at least one additional copy of the sequence into a host cell genome or by integrating an amplifiable selectable marker gene with the polynucleotide, where in the latter case, a cell with the amplified copy of the selectable marker gene and the resulting additional copy of the polynucleotide can be selected by artificially cultivating the cell in the presence of a suitable selectable agent.

Methods well known to those skilled in the art can be used to construct a vector that includes a DNA sequence encoding the GBSS1 mutant polypeptide and an appropriate transcription/translation control signal. The methods include in vitro recombinant DNA technology, DNA synthesis technology, and in vivo recombination technology. The DNA sequence can be effectively linked to an appropriate promoter in a vector to guide mRNA synthesis. The vector may also include a ribosome binding site (RBS) for translation initiation and a transcription terminator.

The vectors applicable in the present disclosure may include commercially available plasmids, such as but not limited to: pBR322 (ATCC37017), pKK223-3 (Pharmacia Fine Chemicals, Uppsala, Sweden), GEM1 (Promega Biotec, Madison, WI, USA), pQE70, pQE60, pQE-9 (Qiagen), pD10, psiX174pBluescript II KS, pNH8A, pNH16a, pNH18A, pNH46A (Stratagene), ptrc99a, pKK223-3, pKK233-3, pDR540, pRIT5 (Pharmacia), pKK232-8, pCM7, pSV2CAT, pOG44, pXT1, pSG (Stratagene), pSVK3, pBPV, pMSG, and pSVL (Pharmacia).

The present disclosure also provides a host cell carrying a nucleic acid sequence, a nucleic acid construct, or an expression vector encoding the GBSS1 mutant polypeptide of the present disclosure. A vector carrying a nucleic acid encoding the protein of the present disclosure is introduced into a host cell, such that the vector exists as a part of a chromosomal integration or exists as a self-replicating extra-chromosomal vector described early, or the vector can achieve gene editing on the endogenous GBSS1 gene of the host cell. The host cell may be any host cell familiar to those skilled in the art, including a prokaryotic cell and a eukaryotic cell.

The nucleic acid sequence, nucleic acid construct, or expression vector of the present disclosure can be introduced into a host cell through a variety of techniques, including transformation, transfection, transduction, viral infection, gene gun or Ti-plasmid-mediated gene delivery, calcium phosphate transfection, DEAE-dextran-mediated transfection, lipofection, electroporation, or the like.

In the production method of the present disclosure, the cells are cultivated on a nutrient medium suitable for the production of the polypeptide by a method well known in the art. If the polypeptide is secreted into the nutrient medium, the polypeptide can be directly recovered from the medium. If the polypeptide is not secreted into the medium, the polypeptide can be recovered from a cell lysate.

The present disclosure has the following advantages:
1. The present disclosure screens out a group of mutant GBSS1 polypeptides.
2. An AC in a plant including the mutant GBSS1 polypeptide of the present disclosure is significantly lower than that in a wild-type plant.
3. The present disclosure also provides a group of mutant GBSS1 polypeptides, and an AC in a plant including the mutant GBSS1 polypeptide is increased by at least 50% compared with an AC in a wild-type plant.

| SEQ ID NO: | Description |
|---|---|
| 1 | Amino acid sequence of Oryza sativa wild-type GBSS1 |
| 2 | Amino acid sequence of P168L mutant GBSS1 |
| 3 | Amino acid sequence of T237A mutant GBSS1 |
| 4 | Amino acid sequence of P168L + T237A mutant GBSS1 |
| 5 | Nucleic acid sequence of P168L mutant GBSS1 |
| 6 | Nucleic acid sequence of T237A mutant GBSS1 |
| 7 | Nucleic acid sequence of P168L + T237A mutant GBSS1 |
| 8 | Nucleic acid sequence of Oryza sativa wild-type GBSS1 |

| SEQ ID NO: | Description |
|---|---|
| 9 | Nucleic acid sequence of L409L base mutation, Nucleic acid sequence encoding mutation of three bases of L at position 409 into cta |
| 10 | Nucleic acid sequence of Q412Q base mutation, Nucleic acid sequence encoding mutation of three bases of Q at position 412 into caa |
| 11 | Nucleic acid sequence of E410E base mutation, Nucleic acid sequence encoding mutation of three bases of E at position 410 into gaa |
| 12 | Nucleic acid sequence of E411K base mutation, Nucleic acid sequence encoding mutation of three bases of E at position 411 into aaa |
| 13 | Amino acid sequence of Q427R mutant GBSS1 |
| 14 | Amino acid sequence of E428G mutant GBSS1 |
| 15 | Amino acid sequence of Q427R + E428G mutant GBSS1 |
| 16 | Nucleic acid sequence of Q427R mutant GBSS1 |
| 17 | Nucleic acid sequence of E428G mutant GBSS1 |
| 18 | Nucleic acid sequence of Q427R + E428G mutant GBSS1 |

DETAILED DESCRIPTION OF THE EMBODIMENTS

The present disclosure will be further explained below in conjunction with examples. The following examples are only preferred examples of the present disclosure, and are not intended to limit the present disclosure in other forms. Any technical personnel familiar with the profession may use the technical content disclosed above to derive equivalent examples through equivalent changes. Any simple modification or equivalent change made to the following examples according to the technical essence of the present disclosure without departing from the content of the solutions of the present disclosure shall fall within the protection scope of the present disclosure.

Figure 1:
FIG. 1 is a schematic diagram of a CBE-nCas9 base editor, where OsU6 and ZmUbi are promoters; sgRNA is a gRNA; bp-NLS is a nuclear localization signal; and NOS is a terminator.
Figure 2:
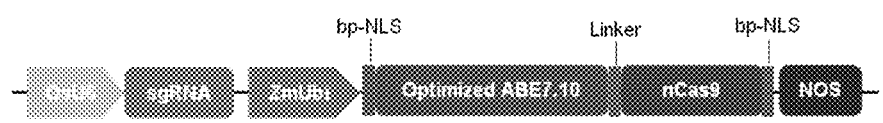
FIG. 2 is a schematic diagram of an ABE-nCas9 base editor, where OsU6 and ZmUbi are promoters; sgRNA is a gRNA; bp-NLS is a nuclear localization signal; and NOS is a terminator.

Example 1 Construction of a Gene Editing Vector and Screening of a Mutation Site 1. A CBE-nCas9 Base Editor (as Shown in FIG. 1) and an ABE-nCas9 Base Editor (as Shown in FIG. 2) Targeting the Endogenous GBSS1 Gene in Oryza sativa were Constructed The CBE base editor could realize the C/G→T/A base conversion within a specified sequence window, and the ABE base editor could realize the A/T→G/C base conversion within a specified sequence window. In the present disclosure, the CBE-nCas9 base editor and the ABE-nCas9 base editor were used as vectors, and several sgRNAs were designed in the Oryza sativa endogenous GBSS1 gene (with sgRNAs shown in Table 1 as examples) and cloned into the CBE-nCas9 and ABE-nCas9 base editor vectors to form several base editors targeting the Oryza sativa endogenous GBSS1 gene. An amino acid encoded by the Oryza sativa endogenous GBSS1 gene was shown in SE ID NO: 1.

TABLE 1

| sgRNA sequences targeting Oryza sativa GBSS1 gene | | |
|---|---|---|
| sgRNA No. | guide-PAM sequence (5'-3') | SEQ ID NO: |
| 1 | GGACCATCCGTCATTCCTGG | 19 |
| 2 | GGCACACTGGCCCACTGGCG | 20 |

TABLE 1-continued sgRNA sequences targeting Oryza sativa GBSS1 gene

| sgRNA No. | guide-PAM sequence (5'-3') | SEQ ID NO: |
|---|---|---|
| 3 | AAGAACAACTACCAGCCCAA | 21 |
| 4 | TCTGCAACGACTGGCACACT | 22 |

2. Oryza sativa Genetic Transformation and Single-Mutant Plant Identification Oryza sativa Xiushui 134 was used as an experimental material. The base editors constructed above were transformed into the Oryza sativa plants by A. tumefaciens to obtain gene-edited plants. The above plants were identified by PCR and sequencing, and it was found that some plants had expected base substitutions within a target range. Specific types of base editing were shown in Table 2.

Dry seeds of each plant in the following table were collected, crushed or ground with a sampler, and dried overnight at 37° C. in an oven. 25 mg of a resulting dry sample powder was taken, 0.5 ml of ethanol was added and then 4.5 ml of 1 N NaOH was added, and a resulting mixture was thoroughly shaken and subjected to a boiling bath for 10 min. A 0.5 ml to 50 ml centrifuge tube was taken, then 25 ml of ddH$_2$O, 0.5 ml of 1 N HAc, and 0.5 ml of an I-KI reagent were added, and a resulting mixture was diluted to 50 ml and then stood for 10 min to enable thorough mixing. The optical density reading at 720 nm was determined by a spectrophotometer, and the AC was calculated according to a fitted equation of a standard curve (with potato amylose samples of Sigma as standard samples). The AC in seeds of each plant (AC (%)) was shown in table 2.

TABLE 2

Mutation types and AC of edited plants

| Plant No. | Base mutation type | Amino acid mutation type | AC (%) |
|---|---|---|---|
| WT | Non-mutated | Wild-type | 19.87 (±0.77) |
| H-410 | C502, 503->T | P168L | 10.60 (±0.85) |
| 199 1-3 | A2515->G | T237A | 13.72 (±0.90) |

As shown in Table 2, the seed ACs of the edited plants H-410 and 199 1-3 were significantly decreased to 50% to 75% of the seed AC of the wild-type plant.

In addition, the above-mentioned seeds with reduced AC were stained by the following method: seeds of normal and edited plants Xiushui 134 were prepared, and glumes were removed from the above seeds to obtain brown rice; the brown rice was cut in half along a back line of the brown rice using a single-sided knife, and an I-KI solution was applied on an exposed endosperm section at a constant dosage; and the endosperm section stood for 10 min and photographed to record a staining result.

Figure 3:
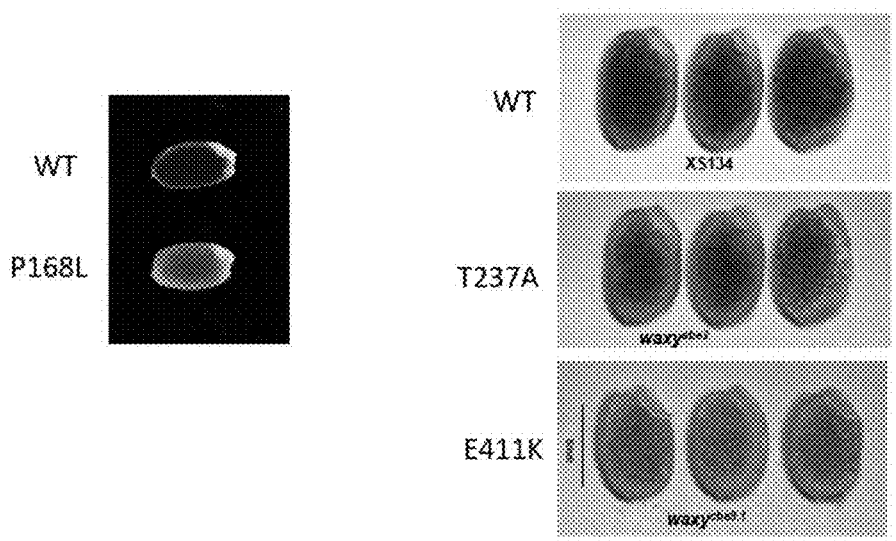
FIG. 3 shows AC observation results of gene-edited seeds (P168L, T237A, and E411K) and wild-type seeds by staining.

Results in FIG. 3 showed that seeds of the edited Oryza sativa were lighter in color than seeds of the wild-type Oryza sativa, indicating that the seeds of the edited Oryza sativa had lower AC.

3. Measurement of AC in Hybrid and Double-Mutant Edited Plants

The H-410 and 199 1-3 plants were crossbred, and the double-mutant plants with P168L and T237A were screened out by PCR and sequencing. The AC was measured according to the above method, and results showed that double-mutant plants with P168L and T237A had significantly-reduced AC.

4. Experimental Conclusion

The mutation of amino acid 168 and/or amino acid 237 of the GBSS1 polypeptide can endow a plant with low AC. The present disclosure has important application values in the cultivation of a GBSS1-mutant crop with low AC.

Example 2 Determination of Relative AC in Other Mutants

With reference to the method in Example 1, the applicants also cultivated Oryza sativa plants of other GBSS1 polypeptide mutation types, and the AC was also determined for homozygous plants (Oryza sativa) of other mutation types. Results were shown in Table 3. The experimental results showed that:

When the mutation occurs at nucleotide positions corresponding to amino acids 409 to 412, the AC of a mutant plant will be greatly reduced. Specifically, mutation types include L409L (three bases encoding L at position 409 are mutated into cta, but such a base change does not result in an amino acid change), E410Q (three bases encoding E at position 410 are mutated into cag), E410K (three bases encoding E at position 410 are mutated into aag), E410E (three bases encoding E at position 410 are mutated into gaa), E411K (three bases encoding E at position 411 are mutated into aaa), and Q412Q (three bases encoding Q at position 412 are mutated into caa). When the nucleic acid sequence undergoes any one of the above mutations, the AC in rice will be significantly reduced to a level of soft rice even if encoded amino acids do not change (for example, L409L, E410E, and Q412Q do not cause an amino acid to change). In addition, when the amino acid 236 is changed from H to R, the AC in rice will also be significantly reduced to the level of soft rice.

When mutations such as G252S (three bases encoding G at position 252 are mutated into agc) or I253V (three bases encoding I at position 253 are mutated into gtc) occur, the AC in rice will be increased.

When mutations such as G252N, N246S, N247D, G393N, and G393S occur, the AC is basically unchanged.

TABLE 3

Results of AC (AC (%)) changes caused by different types of amino acid mutations

| Genotype | amino acid substitution | AC (%) |
|---|---|---|
| waxy$^{abe1}$ | H236R | 1.58 (±0.57) |
| waxy$^{abe2}$ | T237A | 13.72 (±0.90) |
| waxy$^{abe3.1}$ | N246S | 18.41 (±0.34) |
| waxy$^{abe3.2}$ | N247D | 17.80 (±0.42) |
| waxy$^{abe4.1}$ | G252S | 21.41 (±0.47) |
| waxy$^{abe4.2}$ | G252N | 19.34 (±0.86) |
| waxy$^{abe5}$ | I253V | 21.83 (±0.60) |
| waxy$^{abe6}$ | Q389Q | 20.78 (±0.48) |
| waxy$^{abe7.1}$ | A392A/G393N | 19.05 (±0.54) |
| waxy$^{abe7.2}$ | A392A/G393S | 20.51 (±0.50) |
| waxy$^{abe8.1}$ | L409L/E410Q | 2.28 (±0.62) |

TABLE 3-continued

Results of AC (AC (%)) changes caused by
different types of amino acid mutations

| Genotype | amino acid substitution | AC (%) |
|---|---|---|
| waxy$^{abe8.2}$ | L409L/E410K | 0.30 (±0.53) |
| waxy$^{abe9.1}$ | E411K | 2.88 (±0.59) |
| waxy$^{abe9.2}$ | E410E/E411K | 3.06 (±0.26) |
| waxy$^{abe9.3}$ | E410K/E411K/Q412Q | 1.46 (±0.22) |
| XS134 | — | 19.87 (±0.77) |

Example 3 Determination of Other Traits of T237A Mutant

In this example and the drawings, the T237A mutant plant could be represented by waxyabe, and the E411K mutant plant could be represented by waxy$^{abe9, 1}$.

Transparency

Figure 4:
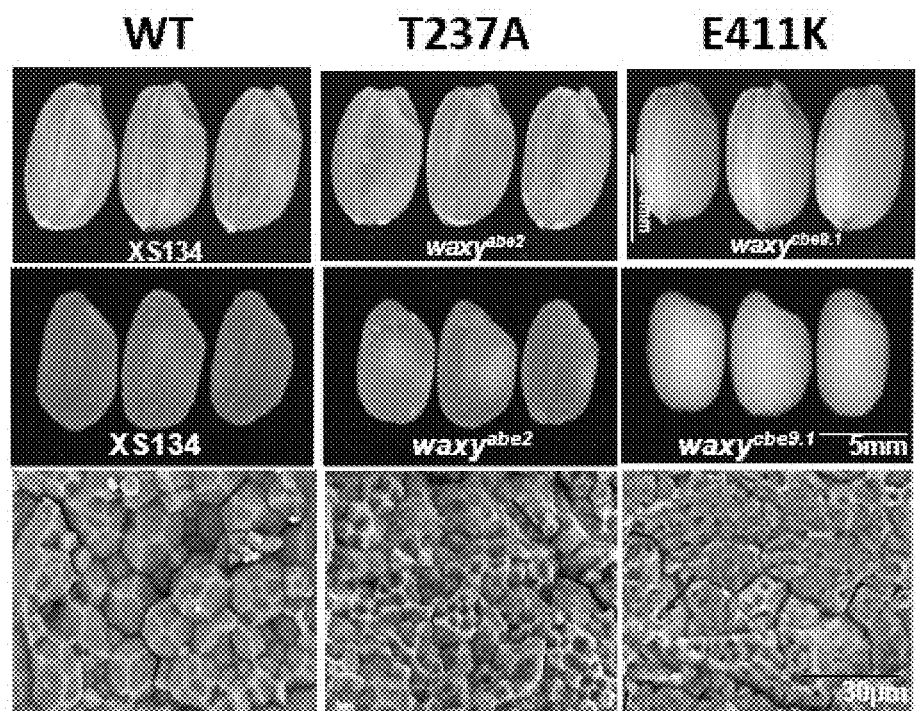
FIG. 4 shows the appearance of rice produced from a wild-type plant, a T237A homozygous mutant plant, and an E411K homozygous mutant plant and the morphology of rice endosperm under a scanning electron microscope.

T237A (three codon bases encoding T at position 237 were mutated into gct) and E411K (AC was basically the same as that of sticky rice) were compared, and it could be found that rice of the E411K mutant plant became white and completely opaque and the phenotype of rice of T237A was similar to that of the wild-type Xiushui 134 (XS134) (as shown in FIG. 4).

The cross-sectional morphologies of the three kinds of rice starch granules were observed using a scanning electron microscope. Endosperm starch granules of T237A and wild-type Xiushui 134 had small particle sizes and showed basically the same morphology, which were all in polygonal shapes with sharp edges and corners, smooth or slightly-concave surfaces, and no structural fragments. However, the starch granules of E411K (sticky rice) were more irregular than the starch granules of the wild-type Xiushui 134 and T237A. In addition, there were many small pores in cores of starch granules in sticky endosperm of E411K (sticky rice), while the starch granules of the transparent wild-type Xiushui 134 and T237A did not have a similar structure (as shown in FIG. 4, the third row of the figure).

Rice GC

Figure 5:
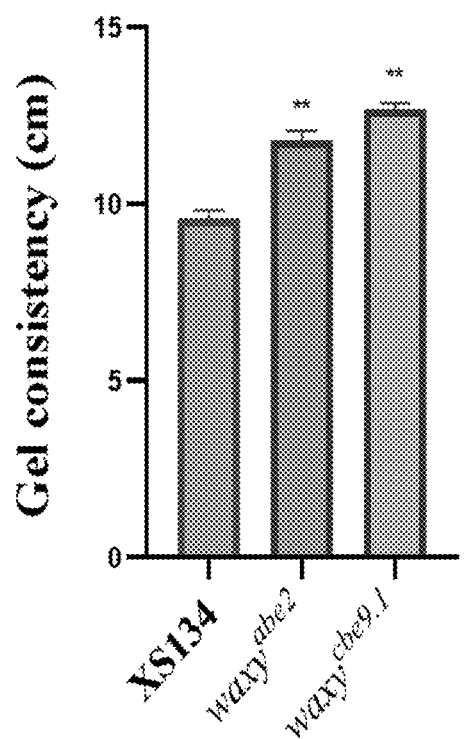
FIG. 5 shows the comparison of gel consistency (GC) of rice endosperm starch among the wild-type plant, the T237A homozygous mutant plant, and the E411K homozygous mutant plant.

Rice GC was measured 4 times according to the measurement method specified in GB/T 22294-2008, and an average was taken. Compared with the wild-type and E411K (sticky rice), the rice GC of T237A was relatively moderate, as shown in FIG. 5.

Viscosity

The viscosity was measured with an RVA instrument (pertentecmaster, Sweden). A sample with a water content of 12% was ground into a flour, and then 3.00 g of the flour was taken and added to 25 ml of distilled water. An RVA procedure was as follows: 50° C. for 1 min; increasing to 95° C. (3.75 min) at a constant rate, and keeping at 95° C. for 2.5 min; and decreasing to 50° C. (3.75 min) at a constant rate, and keeping at 50° C. for 2 min. Data analysis was conducted by TCW 3.0 (Thermal Cycle Win-Dows).

Figure 6:
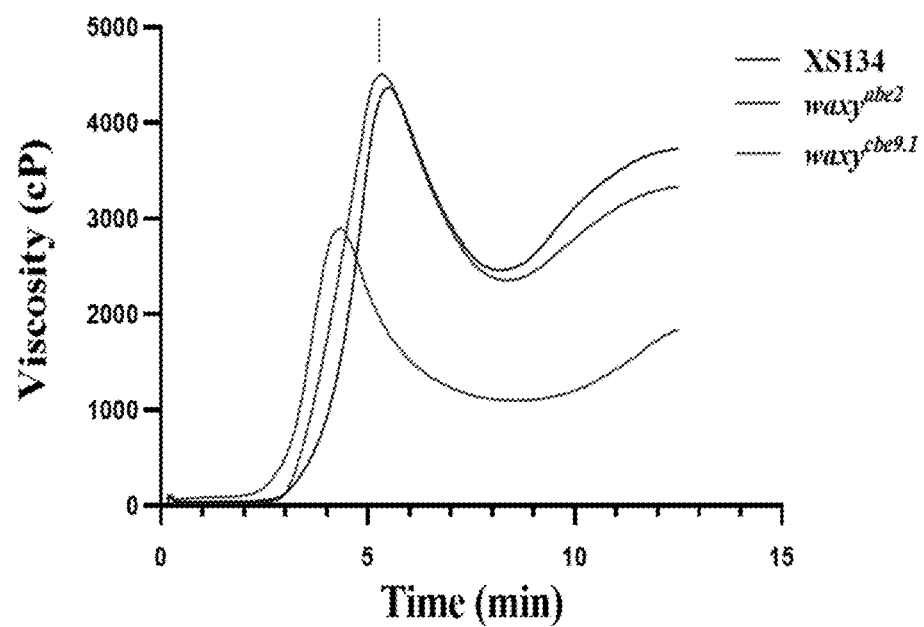
FIG. 6 shows the comparison of rice starch viscosity among the wild-type plant, the T237A homozygous mutant plant, and the E411K homozygous mutant plant.

Compared with the wild-type and E411K, T237A showed a high breakdown (2155.00 cP) and a low setback value (−1177.00 cP), indicating that the T237A mutant rice showed excellent cooking quality (ECQ). Results were shown in FIG. 6.

Rice Size

Figures 7A, 7B, 7C, 7D, 7J:
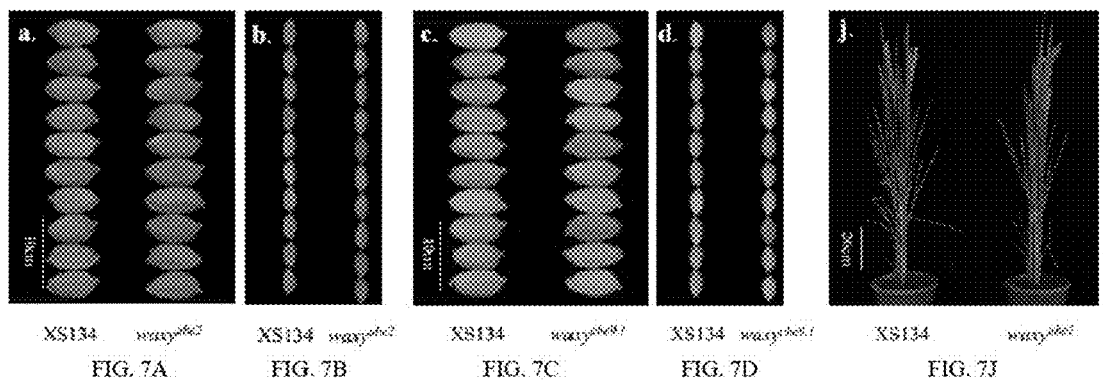
FIG. 7A-FIG. 7J show the comparison of agronomic traits of rice produced by the wild-type plant, the T237A homozygous mutant plant, and the E411K homozygous mutant plant.
Figures 7E, 7F, 7G, 7H, 7I:
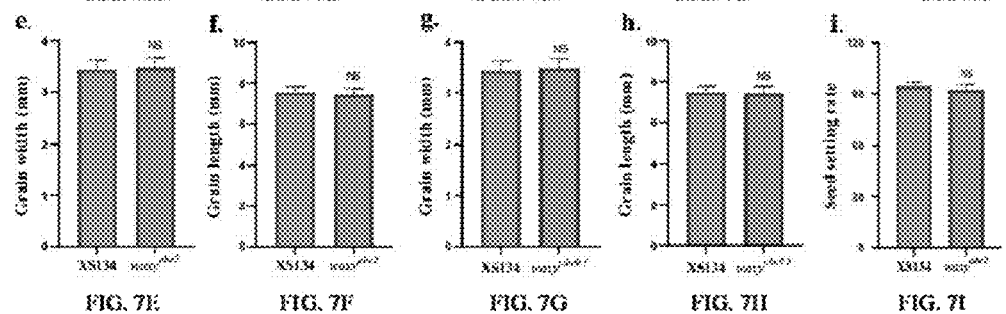

In paddy fields, the T237A and E411K plants showed no significant difference in grain width (FIG. 7A, FIG. 7C, FIG. 7E, and FIG. 7G), grain length (FIG. 7B, FIG. 7D, FIG. 7F, and FIG. 7H), seed setting rate (FIG. 7I), and plant phenotypic traits (FIG. 7J) from the XS134 control.

Experimental results showed that the mutation types of the present disclosure can regulate the AC without affecting other agronomic traits, which is of great significance for cultivating high-quality rice varieties with low AC.

Example 4 Construction of Gene Editing Vectors for Increasing AC and Screening of Mutation Sites 1. sgRNA was designed in the *Oryza sativa* endogenous GBSS1 gene (sgRNA shown in Table 4) and cloned into the ABE-nCas9 vector to form a base editor targeting the *Oryza sativa* endogenous GBSS1 gene. An amino acid sequence encoded by the *Oryza sativa* endogenous GBSS1 gene was shown in SEQ ID NO: 1.

TABLE 4

| sgRNA sequence targeting *Oryza sativa* GBSS1 gene | | |
|---|---|---|
| sgRNA No. | guide-PAM sequence (5'-3') | SEQ ID NO: |
| A-GBSS10 | ATGCAGGAGGACGTCCAGAT | 23 |

2. *Oryza sativa* genetic transformation and transgenic plant identification

*Oryza sativa* Xiushui 134 was used as an experimental material. The base editor constructed above was transformed into the *Oryza sativa* plants by *A. tumefaciens* to obtain gene-edited plants. The above plants were identified by PCR and sequencing, and it was found that some plants had expected base substitutions within a target range. Specific types of base editing were shown in Table 5.

Dry seeds of each plant in the following table were collected, crushed or ground with a sampler, and dried overnight at 37EC in an oven. 25 mg of a resulting dry sample powder was taken, 0.5 ml of ethanol was added and then 4.5 ml of 1 N NaOH was added, and a resulting mixture was thoroughly shaken and subjected to a boiling bath for 10 min. A 0.5 ml to 50 ml centrifuge tube was taken, then 25 ml of ddH$_2$O, 0.5 ml of 1 N HAc, and 0.5 ml of an I-KI reagent were added, and a resulting mixture was diluted to 50 ml and then stood for 10 min to enable thorough mixing. The optical density reading at 720 nm was determined by a spectrophotometer, and the AC was calculated according to a fitted equation of a standard curve (with potato amylose samples of Sigma as standard samples). The AC in seeds of each plant was shown in table 5.

TABLE 5

Mutation types and AC of edited plants

| Plant No. | Base mutation type | Amino acid mutation type | AC |
|---|---|---|---|
| WT | Non-mutated | Wild-type | 18.38% |
| 203-1-3 | A1280 -> G | Q427R | 29.78% |
| 203-1-4 | A1280, 1283 -> G | Q427R, E428G | 25.90% |
| 203-2-2 | A1280 > G | Q427R | 27.25% |
| 203-2-5 | A1283 -> G | E428G | 28.84% |
| 303-2-6 | A1283 -> G | E428G | 26.72% |
| 203-3-3 | A1280, 1283 -> G | Q427R, E428G | 27.84% |
| 203-4-1 | A1280 -> G | Q427R | 27.37% |
| 203-5-1 | A1280 -> G | Q427R | 30.07% |
| 203-5-2 | A1280 -> G | Q427R | 29.13% |
| 203-5-3 | A1280 -> G | Q427R | 28.49% |
| 203-5-5 | A1280 -> G | Q427R | 30.19% |
| 203-5-6 | A1280, 1283 -> G | Q427R, E428G | 29.31% |
| 203-6-2 | A1280 -> G | Q427R | 26.67% |

TABLE 5-continued

Mutation types and AC of edited plants

| Plant No. | Base mutation type | Amino acid mutation type | AC |
|---|---|---|---|
| 203-6-4 | A1280 -> G | Q427R | 28.72% |
| 203-6-5 | A1280 -> G | Q427R | 29.37% |
| 203-6-6 | A1283 -> G | E428G | 27.02% |

As shown in Table 5, the seed AC in an edited plant obtained from the mutation Q427R, the mutation E428G, or the mutation of both was significantly increased compared with the seed AC in the wild-type plant.

In addition, the above-mentioned seeds with increased AC were stained by the following method: seeds of normal and edited plants Xiushui 134 were prepared, and glumes were removed from the above seeds to obtain brown rice; the brown rice was cut in half along a back line of the brown rice using a single-sided knife, and an I-KI solution was applied on an exposed endosperm section at a constant dosage; and the endosperm section stood for 10 min and photographed to record a staining result.

Figure 8:
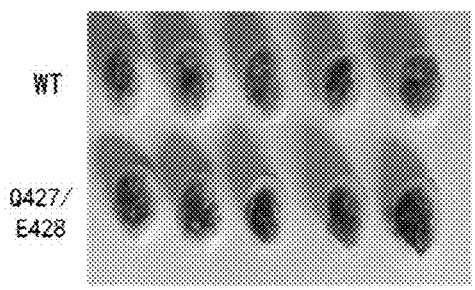
FIG. 8 shows AC observation results of gene-edited seeds (Q427R and E428G) and wild-type seeds by staining.

Results in FIG. 8 showed that seeds of the edited *Oryza sativa* were darker in color than seeds of the wild-type *Oryza sativa*, indicating that the seeds of the edited *Oryza sativa* had higher AC.

3. Experimental Conclusion

The mutation of amino acid 427 and/or amino acid 428 of the GBSS1 polypeptide can endow a plant with high AC. The present disclosure has important application values in the cultivation of a GBSS1-mutant crop with high AC.

All documents mentioned in the present disclosure are cited as references in the present application, as if each document was individually cited as a reference. In addition, it should be understood that various changes or modifications may be made to the present disclosure by those skilled in the art after reading the above teaching content of the present disclosure, and these equivalent forms also fall within the scope defined by the appended claims of the present disclosure.

What is claimed is:

1. A mutant granule-bound starch synthase 1 (GBSS1) polypeptide, wherein compared to an amino acid sequence of a parent GBSS1 as shown in SEQ ID NO: 1, the mutant GBSS1 comprises:
   a mutation at an amino acid corresponding to one or more of amino acid 237 and/or amino acid 168 wherein the amino acid residue 237 is mutated into alanine (A) and/or the amino acid residue 168 is mutated into leucine (L).

2. The mutant GBSS1 polypeptide according to claim 1, wherein the parent GBSS1 is derived from a monocotyledonous plant or a dicotyledonous plant.

3. A polynucleotide encoding a mutant GBSS1 polypeptide, wherein compared to a nucleic acid sequence of a parent GBSS1 as shown in SEQ ID NO: 8, the mutant GBSS1 comprises:
   a mutation encoding an amino acid corresponding to one or more of amino acid 237 and/or amino acid 168, wherein the amino acid residue 237 is mutated into alanine (A) and/or the amino acid residue 168 is mutated into leucine (L).

4. A nucleic acid construct, comprising the polynucleotide according to claim 3 and a regulatory element operably linked to the polynucleotide; wherein the regulatory element is one or more from the group consisting of an enhancer, a transposon, a promoter, a terminator, a leader sequence, a polynucleotide sequence, and a marker gene.

5. A host cell, comprising the mutant GBSS1 polypeptide according to claim 1.

6. A method for changing an amylose content (AC) in a plant or a method for preparing a plant with a changed AC, comprising a step of introducing expression of the mutant GBSS1 polypeptide according to claim 1 into a plant cell, a plant seed, a plant tissue, a plant part, or the plant.

7. A method for reducing an AC in a plant or a method for preparing a plant with a low AC, comprising a step of introducing expression of the mutant GBSS1 polypeptide according to claim 1 into a plant cell, a plant seed, a plant tissue, a plant part, or the plant.

8. The method according to claim 6, wherein the method comprises a step of allowing endogenous GBSS1 of the plant to mutate to introduce the mutant GBSS1 polypeptide.

9. A method of preparing a plant with a changed AC comprising a step of introducing a polynucleotide encoding the mutant GBSS1 polypeptide according to claim 3 into a plant cell, a plant seed, a plant tissue, a plant part, or the plant.

10. A method of preparing a plant with a low AC comprising a step of introducing a polynucleotide encoding the mutant GBSS1 polypeptide according to claim 3 into a plant cell, a plant seed, a plant tissue, a plant part, or the plant.

11. A method for preparing amylose from a plant, wherein the plant is prepared by the method according to claim 6.

12. A plant cell, plant seed, plant tissue, plant part, and plant with a low AC, wherein the plant cell, plant tissue, plant seed, plant part, and plant comprises the mutant GBSS1 polypeptide according to claim 1.

13. The polynucleotide according to claim 3 wherein the parent GBSS1 is derived from a monocotyledonous plant or a dicotyledonous plant.

14. The host cell according to claim 5 wherein the parent GBSS1 is derived from a monocotyledonous plant or a dicotyledonous plant.

15. The mutant GBSS1 polypeptide according to claim 1, wherein the parent GBSS1 is derived from *Oryza sativa*.

16. A host cell, comprising the mutant GBSS1 polynucleotide according to claim 3.

17. A plant cell, plant seed, plant tissue, plant part, and plant with a low AC, wherein the plant cell, plant tissue, plant seed, plant part, and plant comprises the mutant GBSS1 polynucleotide according to claim 3.

18. The polynucleotide according to claim 3, wherein the parent GBSS1 is derived from *Oryza sativa*.

19. The host cell according to claim 5, wherein the parent GBSS1 is derived from *Oryza sativa*.

\* \* \* \* \*